United States Patent
Gulati

(10) Patent No.: US 8,410,148 B2
(45) Date of Patent: Apr. 2, 2013

(54) METHOD AND COMPOSITION FOR POTENTIATING AN OPIATE ANALGESIC

(75) Inventor: Anil Gulati, Naperville, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 12/848,378

(22) Filed: Aug. 2, 2010

(65) Prior Publication Data

US 2010/0311665 A1     Dec. 9, 2010

Related U.S. Application Data

(63) Continuation of application No. 10/301,449, filed on Nov. 21, 2002, now Pat. No. 7,973,064.

(60) Provisional application No. 60/333,599, filed on Nov. 27, 2001.

(51) Int. Cl.
*A61K 31/41* (2006.01)
*A61K 31/40* (2006.01)
(52) U.S. Cl. ......... 514/359; 514/183; 514/408; 514/410
(58) Field of Classification Search .................. 514/183, 514/360, 365, 378, 459, 359, 408, 410
See application file for complete search history.

(56) References Cited

U.S. PATENT DOCUMENTS

| 5,612,539 A | 3/1997 | Hoshi et al. |
| 6,673,832 B1 | 1/2004 | Davar |
| 2002/0082285 A1 | 6/2002 | Lebwohl |
| 2003/0232787 A1 | 12/2003 | Dooley |

FOREIGN PATENT DOCUMENTS

| CA | 2409927 | 12/2001 |
| WO | WO-96/19233 A2 | 6/1996 |
| WO | WO-01/91736 | 12/2001 |

OTHER PUBLICATIONS

Bhalla et al., *Peptides*, pp. 1837-1845 (2002).
Bhargava et al., *The Journal of Pharmacology and Experimental Therapeutics*, 252(3):901-907 (1990).
Davar et al., *NeuroReport*, 9:2279-2283 (1998).
Jarvis et al. *European Journal of Pharmacology*, 388:29-35 (2000).
Wu, *Expert Opinion in Therapeutic Patents*, pp. 1653-1668 (2000).

*Primary Examiner* — Sreeni Padmanabhan
*Assistant Examiner* — Shobha Kantamneni
(74) *Attorney, Agent, or Firm* — Marshall, Gerstein & Borun LLP

(57) ABSTRACT

Composition and methods of treating pain and reducing or reversing tolerance to opiate analgesics are disclosed. The composition and method utilize an opiate analgesic and an endothelin antagonist as active agents to treat pain in mammals, including humans.

8 Claims, 7 Drawing Sheets

Effect of BQ123 pretreatment on analgesia induced by morphine.

METHOD AND COMPOSITION FOR POTENTIATING AN OPIATE ANALGESIC

CROSS-REFERENCE TO RELATED APPLICATIONS

This application is a continuation of application Ser. No. 10/301,449, filed Nov. 21, 2002, pending, which claims the benefit of provisional application Ser. No. 60/333,599, filed Nov. 27, 2001, each incorporated here by reference in their entirety.

FIELD OF THE INVENTION

The present invention relates to the treatment of pain using an opiate analgesic and an endothelin receptor antagonist. More particularly, the present invention relates to a method of potentiating the effects of an opiate analgesic, like morphine, in a mammal by administration of a therapeutically effective amount of an endothelin receptor antagonist. The composition and method permit a reduction in the opiate analgesic dose to provide a desired analgesic effect, without effecting the cataleptic action of the opiate analgesic. The present invention also relates to a method of reducing or reversing tolerance to an opiate analgesic in an individual undergoing opiate analgesic treatment by administering a therapeutically effective amount of an endothelin receptor antagonist. The present composition and methods also reduce the incidence of opiate analgesic addiction.

BACKGROUND OF THE INVENTION

Analgesics are agents that relieve pain by acting centrally to elevate pain threshold, preferably without disturbing consciousness or altering other sensory functions. A mechanism by which analgesic drugs obtund pain (i.e., raise the pain threshold) has been formulated. Research in this area has resulted in the development of a number of opiate and opioid analgesics having diverse pharmacological actions.

The available opiate and opioid analgesics are derivatives of five chemical groups (i.e., phenanthrenes, phenylheptylamines, phenylpiperidines, morphinans, and benzomorphans). Pharmacologically, these opiates and nonopiates differ significantly in activity. Some are strong agonists (morphine), others are moderates-to-mild agonists (codeine). In contrast, some opiate derivatives exhibit mixed agonist-antagonist activity (nalbuphine), whereas others are opiate antagonists (naloxone). Morphine is the prototype of the opiate and opioid analgesics, all of which have similar actions on the central nervous system.

Morphine is an alkaloid chemically derived from opium *papaver somniferum*. Other drugs, such as heroin, are processed from morphine or codeine. Such opiates have been used both medically and non-medically for centuries. By the early 19th century, morphine had been extracted in a pure form suitable for solution. With the introduction of the hypodermic needle, injection of a morphine solution became the common method of administration. Of the twenty alkaloids contained in opium, only codeine and morphine are still in widespread clinical use.

The opiates are among the most powerfully acting and clinically useful drugs producing depression of the central nervous system. Drugs of this group are used principally as analgesics, but possess numerous other useful properties. Morphine, for example, is used to relieve pain, induce sleep in the presence of pain, check diarrhea, suppress cough, ease dyspnea, and facilitate anesthesia.

However, morphine also depresses respiration; increases the activity and tone of the smooth muscles of the gastrointestinal, biliary, and urinary tracts causing constipation, gallbladder spasm, and urinary retention; causes nausea and vomiting in some individuals; and can induce cutaneous pruritus. In addition, morphine and related compounds have other properties that tend to limit their usefulness.

For example, when morphine and related compounds are administered over a long time period, tolerance to the analgesic effect develops, and the dose then must be increased periodically to obtain equivalent pain relief. Eventually, tolerance and physical dependence develop, which, combined with euphoria, result in excessive use and addiction of those patients having susceptible personalities. For these reasons, morphine and its derivatives must be used only as directed by a physician (i.e., not in greater dose, more often, or longer than prescribed), and should not be used to treat pain when a different analgesic will suffice.

Nevertheless, morphine remains the major drug for the treatment of moderate to severe pain (Foley, 1993). Opioids particularly are used to treat conditions lacking a standard treatment, such as cancer pain, trauma, myocardial infarction, post-operative pain, and neuropathic pain. However, opioid painkillers have significant adverse side effects like respiratory depression, nausea, vomiting, dizziness, sedation, mental clouding, constipation, urinary retention, and severe itching.

These adverse side effects limit the usefulness of opioids, like morphins, as painkillers. Therefore, several companies are developing a new generation of opioid painkillers, but advances in neuroscience have not progressed a sufficient extent to provide a significant breakthrough. Typically, companies are using proprietary technology to reformulate opioid drugs, such as morphine, into branded painkillers with improved clinical benefits. To date, innovations in the field of opioid painkillers have largely focused on increasing the convenience of opioid drugs. For example, important advances have been made in opioid delivery, such as sustained release formulations and transmucosal delivery.

The present invention is directed to the discovery that some pharmacological actions of morphine can be modified by coadministration of an endothelin receptor antagonist, hereafter termed an "endothelin antagonist." U.S. patent publication US 2002/0082285 A1 discloses the use of an endothelin antagonist in the treatment of pain.

SUMMARY OF THE INVENTION

The present invention is directed to administration of an endothelin antagonist in combination with an opiate analgesic. More particularly, administration of an opiate analgesic in combination with an endothelin antagonist potentiates the analgesic effect of opioids, and, therefore, lowers the dose of analgesic required to provide a desired pain-reducing effect, without affecting the cataleptic properties of the analgesic. The reduced amount of opiate analgesic required to provide a desired effect reduces the severity of various adverse side effects associated with opiate analgesic treatment.

Accordingly, one aspect of the present invention is to provide a composition comprising an opiate analgesic, e.g., morphine, and an endothelin antagonist for use in treating pain. Such a composition provides a safety factor for the patient because endothelin significantly regulates the autonomic nervous system (A. Gulati et al., (1997); A. Kumar et al. (1997)), and a majority of the withdrawal reactions of morphine also are mediated through the autonomic nervous system. Therefore, endothelin is expected to modulate various pharmacological actions of morphine and other opiate analgesics.

The present invention also is directed to a method of reducing or reversing tolerance to an opiate analgesic in an individual undergoing an opiate analgesic therapy by administering an endothelin antagonist to the individual. In the absence of an administered dose of endothelin antagonist, the opiate analgesic dose would have to be increased over time to achieve the same pain-reducing effect. Administration of an endothelin antagonist allows the opiate analgesic to be administered at a constant, or reduced, dose to achieve a desired pain treatment. The constant or reduced amount of opiate analgesic required to provide a desired pain-reducing effect thus reduces the severity of various adverse side effects associated with opiate analgesic treatment, and reduces the possibility of opiate analgesic dependence.

The present invention also provides a method for improved pain treatment. In particular, the present invention is directed to methods of using an opiate analgesic and an endothelin antagonist to prevent and/or treat pain. More particularly, the present invention is directed to compositions containing morphine and an endothelin antagonist, and to use of an opiate analgesic and endothelin antagonist, administered simultaneously or sequentially, in methods of treating pain and reducing or reversing opiate analgesic tolerance and dependence.

An important aspect of the present invention, therefore, is to provide a method and composition for preventing or treating pain, while reducing the occurrence or severity of adverse side effects associated with opiate analgesic treatment.

Another aspect of the present invention is to reduce the problem of dependence and addiction associated with present opiate analgesics used to treat pain.

Still another aspect of the present invention is to provide a method of reducing or reversing opiate analgesic tolerance in an individual undergoing an opiate analgesic therapy by administering a therapeutically effective amount of an endothelin antagonist to the individual.

Yet another aspect of the present invention is to provide an article of manufacture for human pharmaceutical use, comprising (a) a package insert, (b) a container, and either (c1) a packaged composition comprising an opiate analgesic and an endothelin antagonist or (c2) a packaged composition comprising an opiate analgesic and a packaged composition comprising an endothelin antagonist.

These and other aspects of the present invention will become apparent from the following detailed description of the preferred embodiments of the invention.

DETAILED DESCRIPTION OF THE PREFERRED EMBODIMENTS

Figure 1:
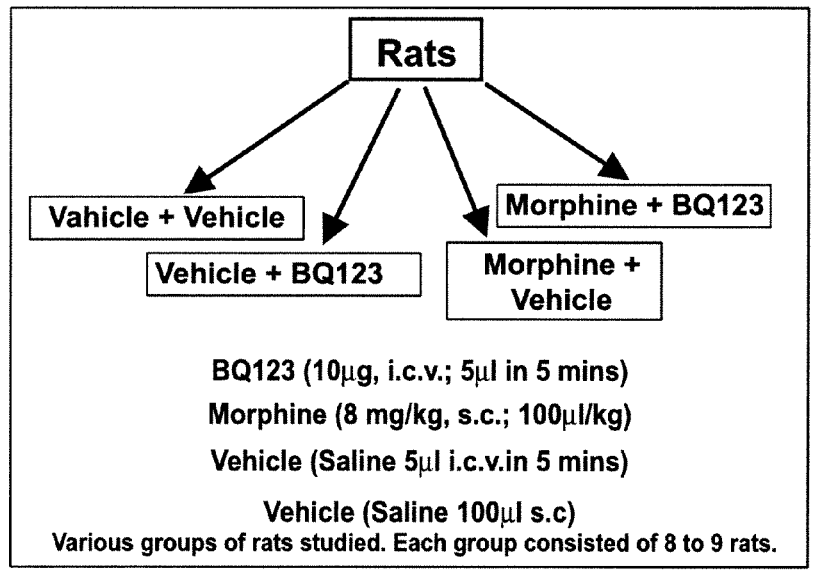
FIG. 1 illustrates an example of the groups of rats treated with a vehicle, endothelin antagonist, morphine, and endothelin antagonist plus morphine.

The present invention is directed to the simultaneous or sequential administration of an opiate analgesic and an endothelin antagonist to prevent and/or treat pain. In particular, the administration of morphine and an endothelin antagonist to rats and mice show that the endothelin antagonist potentiates the analgesic effect of morphine, and, therefore, the dose of morphine can be reduced, while providing an analgesic effect equivalent to administering a higher dose of morpholine alone. Such a coadministration of active agents does not effect the cataleptic properties of morphine. The reduced dose of morphine also reduces adverse side effects associated with morphine administration, and can significantly reduce the addiction potential of morphine in susceptible individuals.

The present invention also is directed to the administration of an endothelin antagonist to an individual undergoing an opiate analgesic therapy to reduce or reverse opiate analgesic tolerance in the individual. The administration of an endothelin antagonist allows the dose of opiate analgesic to remain constant, or to be reduced, while maintaining the desired pain-reducing effect. By reducing or reversing tolerance to an opiate analgesic, the occurrence of adverse side effects can be reduced, and the possibility of opiate analgesic dependence is reduced.

The present invention, therefore, provides compositions and methods of potentiating the analgesic properties of an opiate analgesic, and of reducing or reversing tolerance to opiate analgesics. The present invention also provides pharmaceutical compositions comprising an opiate analgesic and an endothelin antagonist. Further provided are articles of manufacture comprising an opiate analgesic and an endothelin antagonist, packaged separately or together, and an insert having instructions for using the active agents.

The methods described herein benefit from the use of an opiate analgesic and an endothelin antagonist in the treatment and management of pain. The analgesic and antagonist can be administered simultaneously or sequentially to achieve the desired effect of pain treatment or reduction or reversal of opiate analgesic tolerance.

For the purposes of the invention disclosed herein, the term "treatment" includes preventing, lowering, or eliminating pain. As such, the term "treatment" includes both medical therapeutic and/or prophylactic administration, as appropriate.

The term "cataleptic" is defined herein as a trance-like condition wherein a mammal's limbs remain in any position in which they are placed, and there is an apparent loss of sensation and awareness.

The term "container" means any receptacle and closure therefore suitable for storing, shipping, dispensing, and/or handling a pharmaceutical product.

The term "insert" means information accompanying a product that provides a description of how to administer the product, along with the safety and efficacy data required to allow the physician, pharmacist, and patient to make an informed decision regarding use of the product. The package insert generally is regarded as the "label" for a pharmaceutical product.

The phrase "reducing or reversing opiate analgesic tolerance" is defined as the ability of a compound to reduce the dosage of an opiate analgesic administered to an individual to maintain a level of pain control previously achieved using a greater dosage of opiate analgesic.

Several neurotransmitter mechanisms have been proposed as playing a role in the action of morphine and morphine tolerance and dependence. Evidence exists that a central endothelin (ET) mechanism is involved in the actions of morphine. It has been found that ET antagonists, including BQ123, for example, can potentiate morphine-induced analgesia and hyperthermia without affecting catalepsy. The present invention, therefore, provides a novel method of managing pain, reducing dependence on opioids, and reducing tolerance to opioids.

Pharmacological agents can control most pain, but it is essential to select the correct analgesic for the individual. Morphine is a major drug for the treatment of moderate to severe pain (Foley, 1993). Morphine primarily is used to treat severe pain associated with trauma, myocardial infarction, and cancer. The use of morphine in the treatment of chronic pain is limited because of inadequate analgesia, for example. Although, morphine is one of the most effective painkillers, effective pain management requires that adequate analgesia be achieved without excessive adverse side effects. Many patients treated with morphine are not successfully treated because of excessive adverse side effects and/or inadequate analgesia.

Management of excessive adverse side effects associated with morphine administration remains a major clinical challenge. Numerous strategies have been advanced to address this problem, such as (i) switching opioids, (ii) switching routes of opioid administration, (iii) improved opioid formulations, (iv) clonidine treatment, and (v) coadministrating opioids that act on different receptors.

A massive research effort directed to the development of opioid analgesics, resulted in the discovery of numerous compounds having a varying affinity and efficacy at all the known opioid receptor subtypes. Although compounds of extremely high potency have been produced, the problem of tolerance to, and dependence on, these agonists persists (Williams et al., 2001).

For example, the chronic administration of morphine results in the development of physical dependence, as evidenced by the appearance of distressing physical symptoms induced by abrupt termination of morphine treatment. The signs and symptoms simulate a severe cold, and usually include nasal discharge, lacrimation, chills, goose pimples, muscular aches, enhanced motor reflexes, profound body water loss attributed to hyperthermia, hyperventilation, emesis, and diarrhea (Himmelsbach, 1943; Katz et al., 1986; Maldonado et al., 1996; Quock et al., 1968). It is well known that various types of opioid receptors are involved in the development of the psychological and physical dependence on opioids.

The opioid receptors have been classified as µ, δ, and κ receptors, based on the relative affinity shown for experimental opioid receptor ligands. µ-Opioid receptors have been reported to play a dominant role in several pharmacological effects of morphine.

Role of µ-Opioid Receptors

An intracerebroventricular (i.c.v) injection of a selective and irreversible µ-opioid receptor antagonist, i.e., β-funaltrexamine (β-FNA), drastically antagonizes morphine induced antinociception (Portoghese et al., 1980; Takemori et al., 1981; Ward et al., 1982). β-FNA also inhibits the development of physical dependence on morphine in rats (Aceto et al., 1986; DeLander et al., 1984). Administration of a selective µ-opioid receptor antagonist, i.e., D-Phe-Cys-Tyr-D-Trp-Arg-The-Pen-Thr-$NH_2$, into the lateral cerebral ventricle 72 hours after subcutaneous implantation of two 75 mg pellets of morphine in rats induces a severe withdrawal syndrome (Maldonado et al., 1992). The knockout mice with deleted µ-opioid receptors display no expression of naloxone-precipitated withdrawal symptoms including jumping and body weight loss (Matthes et al., 1996). It has been demonstrated that µ-opioid receptors consist of $µ_1$ and $µ_2$ subtypes in the central nervous system (CNS) (Goodman et al., 1985). The irreversible $µ_1$-opioid receptor antagonist naloxonazine (Pasternak et al., 1980) is useful in investigating the function of $µ_1$-opioid receptors. The CXBK recombinant inbred strain of mouse is deficient in $µ_1$-opioid receptors, and is much less sensitive than C57BL/6 progenitor strain to the antinociceptive and locomotor effects of morphine (Moskowitz et al., 1985). In addition, the incidence of naloxone-precipitated jumping is much less in morphine-dependent C57BL/6 mice (Suzuki et al., 1992a). The naloxone-induced body shakes also occurred at lower doses in C57BL/6 that in CXBK mice.

Role of δ-Opioid Receptors

Studies suggest that an interaction exists between µ- and δ-opioids. It has been found that at subantinociceptive doses, δ-opioid receptor agonists modulate antinociceptive responses to µ-opioid receptor agonists in mice (Jiang et al., 1990). Morphine acts mainly at the µ-receptor sites, but also can interact with δ-opioid receptors in vivo and in vitro (Narita et al., 1993). δ-Opioid receptor antagonists do not effect morphine antinociceptive action. However, the selective blockade of δ-opioid receptors by naltrindole (NTI) inhibits the development of physical dependence on morphine (Suzuki et al., 1997).

Role of κ-Opioid Receptors

Increasing evidence indicates that activation of κ-opioid receptor opposes a variety of µ-opioid receptor mediated actions throughout the brain and spinal cord (Pan, 1998). Treatment with nor-binaltorphimine (nor-BNI), a selective κ-opioid receptor antagonist, when compared to naloxone, did not precipitate weight loss or other withdrawal signs in morphine-dependent mice (Cowan et al., 1988). Pretreatment with nor-BNI during chronic morphine treatment displays aggravation of the weight loss precipitated by naloxone in morphine-dependent mice and rats (Suzuki et al., 1992b). These studies indicate that antagonism of endogenous κ-opioidergic system apparently elicits a potentiating effect on some morphine-withdrawal signs, including weight loss. Stimulation of endogenous κ-opioidergic system therefore should attenuate morphine withdrawal symptoms. Dynorphin A has been reported to inhibit morphine withdrawal symptoms induced by naloxone precipitation or morphine discontinuation in morphine dependent animals (Suzuki et al., 1992a). However, 3,4-dichloro-N-methyl-N-[2-(1-pyrrolidinyl)cyclohexyl]benzeneacetamide (i.e., U-50,488H), a selective κ-opioid receptor agonist, did not suppress the development of physical dependence on morphine in rats (Fukagawa et al., 1989). This difference has been attributed to the action of dynorphin A on all three subtypes of κ-opioid receptors, while U-50,488H acts mainly on $κ_1$-opioid receptor subtype (Narita et al., 2001).

In summary, µ- and δ-opioid receptors show morphine-like withdrawal symptoms, while κ-opioid agonists do not. An opposing interaction occurs between µ/δ-opioid agonists and κ-opioid agonists.

Role of Nonopioid Receptors in Morphine Actions

Numerous studies, including molecular and genetic approaches, suggest a substantial role of µ-opioid receptors in the development of morphine dependence and in numerous other actions of morphine. However, other systems also are involved. A role for 5-HT and cholecystokinin systems, as well as N-methyl-D-aspartate (NMDA) receptors, in opioid place conditioning has been proposed (Van Ree et al., 1999).

It has been widely reported that prototypical NMDA receptor antagonists dizocilpine and ketamine, which have similar affinity for NR1/NR2A and NR1/NR2B receptors (Varney et al., 1996), suppress morphine-induced place preference (Avenet et al., 1997; Tzschentke et al., 1995). Evidence is accumulating that the NR2B subunit of NMDA receptors in the nucleus accumbens may be involved in the rewarding effect of morphine (Standaert et al., 1994; Watanabe et al., 1993). Neuroadaptive changes in specific brain regions that generate opioid dependence have been identified as noradrenergic trans-mission originating in the locus ceruleus, and most likely play the primary causal role in the expression of physical dependence on opioids. In contrast, a combination of behavioral and neurobiological studies point to the mesolimbic dopaminergic pathway projecting from the ventral tegmental area to the nucleus accumbens as a critical site for the initiation of psychological dependence on opioids.

Endothelin in the Central Nervous System

ET is an extremely potent endothelium derived vasoconstriction factor (Hickey et al., 1985) that was isolated, sequenced, and cloned (Yanagisawa et al., 1988). Endothelins are 21 amino acid, highly potent vasoconstrictive peptides with two disulfide bonds. Endothelins are produced biologically by enzymatically cleaving preproendothelin to proendothelin, then to endothelin by endothelin-converting enzymes. ET exerts biological effects by binding to cell surface receptors which are 7-trans-membrane receptors coupled to G-proteins. There are two distinct types of endothelin receptors, (a) the ET-1 selective $ET_A$ receptors primarily found on vascular smooth muscle and responsible for vasoconstriction, and (b) nonselective $ET_B$ receptors primarily found in vascular endothelium and responsible for vasodilation.

The vasoconstrictive effects of ET-1 are mediated predominantly by G-protein coupled $ET_A$ receptors (Reynolds et al., 1989). ET-1 also is made in high concentrations by prostate, metastatic cancers, and CNS. ET in the CNS is produced by endothelial cells and nonendothelial cells, such as neurons, astrocytes, and glial cells (MacCumber et al., 1990).

The global distribution of ET and its binding sites in the brain suggests that, in addition to being a vasoconstrictor, it may be acting as an important neuropeptide in the CNS (Gulati et al., 1992). Endothelin (ET) receptor antagonists, in particular selective $ET_A$ or balanced antagonists $ET_A/ET_B$, represent a therapeutic area for diseases such as congestive heart failure (CHF) and pulmonary hypertension. BQ-123 and BMS-182874 are specific antagonists of $ET_A$ receptors (Ihara et al., 1992; Stein et al., 1994). Endothelin antagonists have profound effects on the pulmonary vasculature and the right heart, whereas ACE inhibitors primarily affect the peripheral vessel and the left heart.

Several studies indicate that the central ET receptors are predominantly of $ET_B$ subtype (Matsumura et al., 1991). Rat cerebral astrocytes have been shown to express mainly $ET_B$ type of receptors (Hama et al., 1992) and glial cells also were found to intensely express $ET_B$ receptor mRNA (Pagotto et al., 1995). However, the central administration of a highly selective $ET_B$ receptor agonist, IRL-1620, does not produce any effect on the cardiovascular system, and the systemic and regional circulatory effects of centrally administered ET-1 have been shown to be mediated through the $ET_A$ receptors (Gulati et al., 1995; Rebello et al., 1995).

Intracerebroventricular administration of ET-1 produces a transient rise followed by sustained fall in the mean arterial blood pressure (BP) (Gulati et al., 1996). The pressor effect was accompanied by an increase in renal sympathetic nerve activity and plasma levels of catecholamines and arginine-vasopressin (Matsumura et al., 1991).

It also has been shown that the effects of central administration of ET-1 are mediated through activation of the sympathetic nervous system because these effects were attenuated by ganglion blockers (Kawano et al., 1989; Matsumura et al., 1991). Intracisternal administration of ET-1 elicited a transient increase in BP, renal sympathetic nerve activity, and phrenic nerve activity. A subsequent fall in BP was accompanied by a decrease in renal sympathetic nerve activity and phrenic nerve activity (Kuwaki et al., 1994). The observation that central ET-1 induced increase in pressor response was suppressed by pretreatment with phenoxybenzamine (Ouchi et al., 1989), further implicates the active participation of sympathetic nervous system in the initial pressor phase.

Interaction of Opioids and Endothelin

Both ET and opioids exist in the CNS and can play a role in regulation of cardiovascular and/or other functions. These two peptides can have some interactions, especially through the sympathetic nervous system because both are located in sites involved in cardiovascular regulation, such as, for example, the hypothalamus, nucleus tractus solitarius, and locus ceruleus. Very few studies exist indicating that ET and opioids interact and modulate the effects of one another.

For example, it has been reported that ET can induce pain, which can be blocked by morphine. ET-1 administered intraperitoneally into Cr1:CD-1(ICR)BR mice and CXBK mice produced abdominal irritation which produced a single occurrence of a wave of constriction and elongation passing caudally along the abdominal wall accompanied by a mild twisting of the trunk followed by extension of the hind limbs. This ET-1 induced nociception could be blocked by morphine through $\mu_1$ sensitive pathway (Raffa et al., 1994). In another study, ET-1 (200 to 800 µM) applied to rat sciatic nerve produced reliable, robust, unilateral hindpaw flinching lasting for 60 min. Pretreatment with morphine completely blocked this effect in a naloxone sensitive manner. BQ123, an $ET_A$ receptor antagonist, also blocked the ET-1 induced hind paw flinching (Davar et al., 1998). The role of $ET_A$ receptor antagonist ABT-627 in tactile allodynia has been investigated in streptozotocin-induced diabetic rat model of neuropathic pain.

The systemic administration of ABT-627 produced a dose-dependent increase (40 to 50%) in tactile allodynia thresholds. The antinociceptive effect of ABT-627 was maintained following chronic administration of the antagonist in drinking water for 7 days. In comparison, morphine produced a significant (90%) increase in tactile allodynia thresholds. $ET_B$ receptor antagonist did not affect the tactile allodynia threshold (Jarvis et al., 2000).

Responses to morphine can be associated with increased systemic and cerebrovascular levels of ET-1 and upregulation of ET-1 and $ET_A$ receptor mRNA in the brainstem of newborn piglets (Modanlou et al., 1998). ET-1 administered intracerebroventricularly (i.c.v.) caused significant increases in mean arterial pressure and RSNA, and these effects were potentiated by naloxone pretreatment (Matsumura et al., 1994). The effect is centrally mediated because naloxone methobromide, a naloxone derivative that does not cross the blood-brain barrier, did not alter the baroreflex sensitivity. It was concluded that ET-1 exerts a potent central pressor action mediated by enhanced sympathoadrenal outflow, and naloxone potentiates these pressor and sympathetic responses.

In accordance with an important feature of the present invention, it has been hypothesized that actions of morphine and related opioids mediated through the sympathetic pathway can be modulated by ET antagonists, and that an interaction exists between opioids and ET. This approach is particularly useful for the management of symptoms of morphine withdrawal.

In accordance with another important feature of the present invention, an opiate analgesic is present in a composition, or is administered, with an endothelin antagonist in a weight ratio of analgesic-to-antagonist of about 0.01:1 to about 100:1, preferably about 0.02:1 to about 50:1, and most preferably about 0.1:1 to about 10:1. This ratio depends upon the type and identity of opioid analgesic and endothelin antagonist being used. The ratio of analgesic-to-antagonist that is administered is dependent upon the particular analgesic and antagonist used, and the origin and severity of the pain being treated. This ratio can be readily determined by a person skilled in the art to achieve the desired reduction in pain.

An opiate analgesic utilized in the present invention can be one or more opium alkaloid or semisynthetic opiate analgesic. Specific opiate analgesics include, but are not limited to, (a) opium; (b) opium alkaloids, such as morphine, morphine sulfate, codeine, codeine phosphate, codeine sulfate, diacetylmorphine, morphine hydrochloride, morphine tartrate, and diacetylmorphine hydrochloride; and (c) semisynthetic opiate analgesics, such as dextromethorphan hydrobromide, hydrocodone bitartrate, hydromorphone, hydromorphone hydrochloride, levorphanol tartrate, oxymorphone hydrochloride, and oxycodone hydrochloride. Other opioids include, but are not limited to, fentanyl, meperidine, methodone, and propoxyphene.

An endothelin antagonist utilized in the present invention can be any of the endothelin receptor antagonists known in the art. Endothelin is a potent vasoconstrictor. Endothelin antagonists are used to treat acute heart failure, congestive/chronic heart failure, pulmonary arterial hypertension, pulmonary edema, subarachnoid hemorrhage, chronic obstructive pulmonary disease, myocardial infarction, acute cerebral ischemia, acute coronary syndromes, acute renal failure, post-operative treatment in liver operations, and prostate cancer.

No adverse effects are expected when a healthy patient is administered an opiate analgesic in combination with an endothelin antagonist. However, for patients suffering from conditions like congestive heart failure and other diseases treatable by an endothelin antagonist, coadministration of an opioid analgesic and an endothelin antagonist should be monitored carefully.

Preferred ET antagonists are antagonists selective for endothelin A ($ET_A$) receptors or are balanced $ET_A$/endothelin B ($ET_B$) antagonists. Such ET antagonists are set forth in Appendices A and B herein. However, endothelin B antagonists and miscellaneous endothelin antagonists, as set forth in Appendices C and D herein, also can be used in a composition or method of the present invention. Additional useful endothelin antagonists can be found in U.S. Patent Application Publication No. US 2002/0082285 A1, incorporated herein by reference.

Specific examples of endothelin antagonists useful in the present invention include, but are not limited to, atrasentan, tezosentan, bosentan, sitaxsentan, enrasentan, BMS-207940 (Bristol-Myers Squibb), BMS-193884, BMS-182874, J-104132 (Banyu Pharmaceutical), VML 588/Ro 61-1790 (Vanguard Medica), T-0115 (Tanabe Seiyaku), TAK-044 (Takeda), BQ-788, BQ123, YM-598, LU 135252, PD 145065, A-127722, ABT-627, A-192621, A-182086, TBC3711, BSF208075, S-0139, TBC2576, TBC3214, PD156707, PD180988, ABT-546, ABT-627, Z1611, RPR118031A, SB247083, SB217242, S-Lu302872, TPC10950, and SB209670.

BQ123 is a specific endothelin A antagonist, and is the sodium salt of cyclo(-D-Trp-D-Asp-Pro-D-Val-Leu-). BQ-788 is a specific endothelin B antagonist, and is the sodium salt of N-cis-2,6-dimethylpiperidinocarbonyl-L-gamma-methylleucyl-D-1-methoxycarbonyl triptophanyl-DNle (see *Proc. Natl. Acad. Sci. USA*, 91, pp. 4892-4896 (1994)).

In addition to a conventional endothelin antagonist, a compound that inhibits the formation of endogenous endothelin also can be used as the endothelin antagonist in the present invention. Such compounds are useful because they prevent endothelin formation, and, therefore, decrease the activity of endothelin receptors. One class of such compounds is the endothelin converting enzyme (ECE) inhibitors.

Useful ECE inhibitors include, but are not limited to, CGS34225 (i.e., N-((1-((2(S)-(acetylthio)-1-oxopentyl)-amino)-1-cyclopentyl)-carbonyl-S-4-phenylphenyl-alanine methyl ester) and phosphoramidon (i.e., N-(a-rhamnopyranosyloxyhydroxyphosphinyl)-Leu-Trp).

The following tests were conducted to illustrate the potentiating effects of an endothelin antagonist on an opiate analgesic administered to a mammal, including humans.

Male Sprague-Dawley rats weighing 225 to 250 g (Sasco King Animal Co., Madison, Wis.) were housed in a room with controlled temperature (23±1° C.), humidity (50±10%), and light (6:00 a.m. to 6:00 p.m.) for at least four days prior to testing. Food and water were available to the rats continuously.

The rats were divided into four groups (FIG. 1): group 1 received vehicle (saline 5 μl, i.c.v. over 5 minutes) and vehicle (saline 100 μl/kg s.c.); group 2 received vehicle (saline 100 μl/kg, s.c.) and BQ123 (10 μg, i.c.v. in a volume of 5 μl over 5 minutes); group 3 received morphine (8 mg/kg, s.c. in a volume of 100 μl/kg) and vehicle (saline 100 μl/kg, s.c.); and group 4 received morphine (8 mg/kg, s.c. in a volume of 100 μl/kg) and BQ123 (10 μg, i.c.v. in a volume of 5 μl over 5 minutes). Vehicle or BQ123 treatment was performed 30 minutes prior to morphine administration.

Tests also were performed on mice. The mice were housed and fed similar to the rats as described above taking into consideration the size differential between rats and mice. The mice were divided into groups identical to the rats, but administered different amounts of vehicle, opiate analgesic, and endothelin antagonist, as disclosed hereafter.

Measurement of analgesic effect: The analgesic response to morphine was determined by the tail flick method. The tail flick latencies to thermal stimulation were determined before and 30, 60, 90, 120, 180, 210, 240, 270, 300, and 360 minutes after the morphine injection. The basal tail flick latency was about 2 seconds. A cutoff time of 10 seconds was used to prevent damage to the tail. The basal latency was subtracted from that induced by morphine. The analgesic response in each rat was converted into $AUC_{0 \rightarrow 360\ min.}$ (area under the curve), and was expressed as mean±SEM. Eight to nine animals were used for each dose of morphine sulfate. The differences in analgesic response to different doses of morphine were compared by using student's t test. A value of $P<0.05$ was considered significant.

Measurement of colonic temperature: The change in temperature in response to morphine was determined. The colonic temperature of each rat was recorded before and various times after morphine injection for a period of 360 minutes using a telethermometer. The change in temperature from the basal value was plotted with time and was converted to $AUC_{0 \rightarrow 300\ min.}$ and was expressed as mean±SEM. Eight to nine rats were used for each dose of morphine sulfate. Rats used to measure tail flick latencies also were used to determine the colonic temperature. The differences in temperature response between various groups were compared by using student's t test. A value of $P<0.05$ was considered significant.

Measurement of catalepsy: Rats were tested for catalepsy by the bar test. An aluminum bar 5 mm in diameter was placed 4 cm above the floor, and the animal's forepaw was gently placed on the bar. The time required for the animal to place at least one paw on the floor was measured with a maximum term of observation of 180 seconds. Behavioral evaluation of catalepsy was performed 45 minutes after the administration of morphine or its vehicle. Statistical tests were performed as described above.

Effect on body weight: Body weight was measured in all groups of rats of FIG. 1. BQ123 pretreatment induced no change in body weight between the four test groups. Body weight was measured before administering any drug and at the end of the experiment, i.e., seven hours after the administration of morphine. The data clearly indicates that all groups were very comparable in their response to change in body weight, and that neither morphine nor BQ123 produced any acute effect on body weight.

Effect on cataleptic behavior: Morphine administration significantly increased catalepsy in rats. In contrast, BQ123 did not produce any cataleptic effect. Catalepsy is an overall indication of motor behavior including locomotor activity of rats. Pretreatment with BQ123 did not produce any change in morphine-induced catalepsy. In particular, morphine produced a significant increase in catalepsy compared to control group 1, but this increase in catalepsy was not affected by BQ123 pretreatment. Therefore, the effect of morphine on cataleptic behavior was not affected by administration of the endothelin antagonist BQ123. These findings indicate that BQ123 did not affect a pharmacological action produced in rats by morphine.

Effect on body temperature: The control treated rats (group 1 of FIG. 1) did not show any effect on body temperature. BQ123 treatment also did not produce any significant effect on body temperature. Morphine treatment produced significant hyperthermia in rats. Hyperthermia lasted for about four hours after the administration of morphine. The hyperthermic effect of morphine was significantly potentiated by BQ123. The hyperthermic effect of morphine was not only significantly greater in BQ123 pretreated rats, but lasted for more than six hours. In particular, it was demonstrated that morphine produced a significant increase in body temperature compared to control group 1. Pretreatment with BQ123 significantly potentiated the effect of morphine-induced hypothermia compared to vehicle and morphine-treated rats. This is a significant observation because although morphine-induced catalepsy is not affected by endothelin antagonist BQ123, the hyperthermic response to morphine is potentiated by BQ123.

Figure 2:
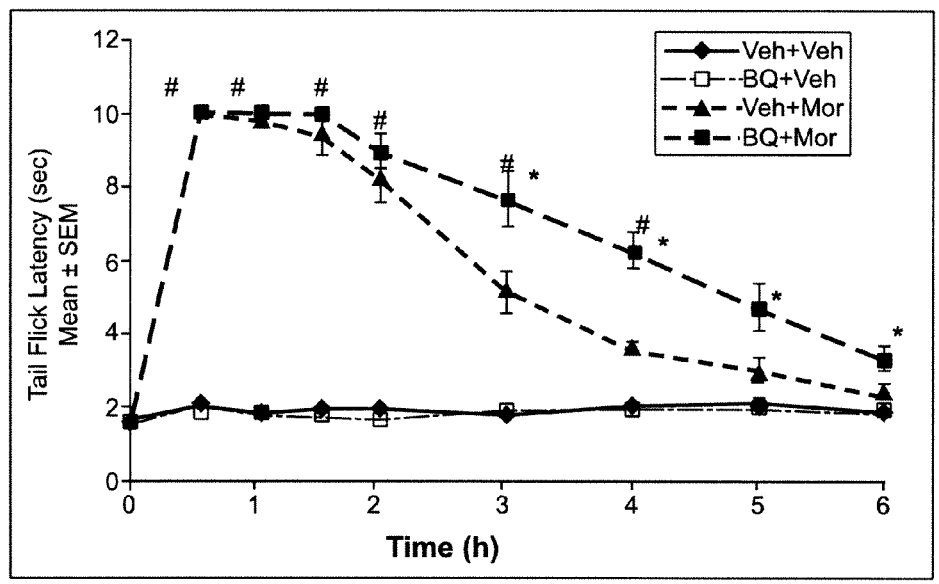
FIG. 2 contains plots for the effect of BQ123 pretreatment on analgesia induced by morphine for four groups of treated rats.

Effect on analgesia: The control group of rats exhibited tail flick latencies of about 2 seconds. BQ123 treatment did not produce any significant effect on tail flick latency. Morphine (8 mg/kg, s.c.) produced significant analgesia in rats, and the tail flick latencies reached more than 10 seconds (FIG. 2). A significant increase in tail flick latencies was observed until three hours after the administration of morphine. The analgesic effect of morphine was significantly potentiated by BQ123. The analgesic effect of morphine not only was significantly greater in BQ123 pretreated rats, but lasted for more than six hours.

Figure 3:
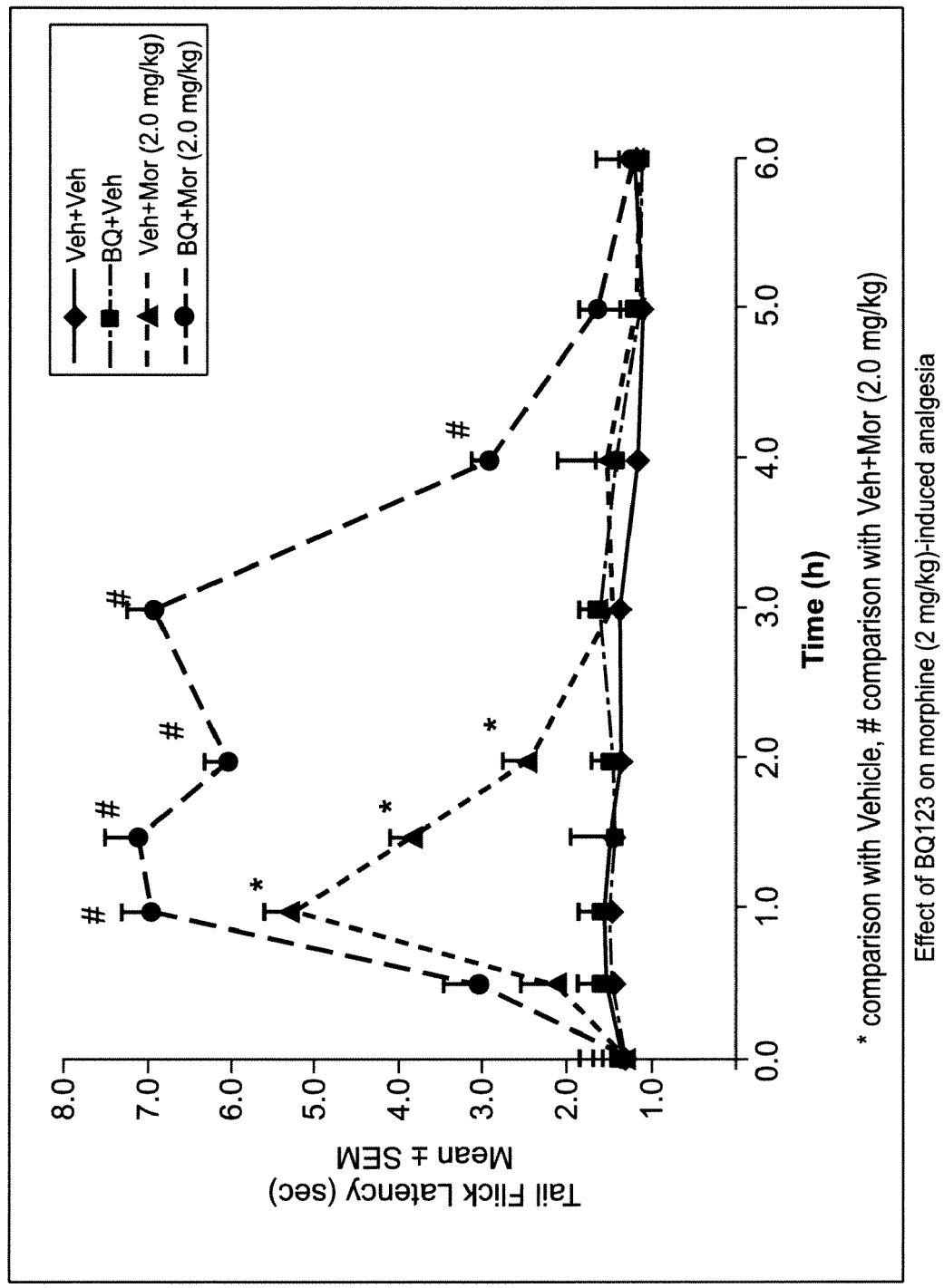
FIGS. 3-5 contain plots for the effect of BQ123 pretreatment on analgesia induced by morphine (2, 4, and 8 mg/kg, respectively), for four groups of treated mice.
Figure 4:
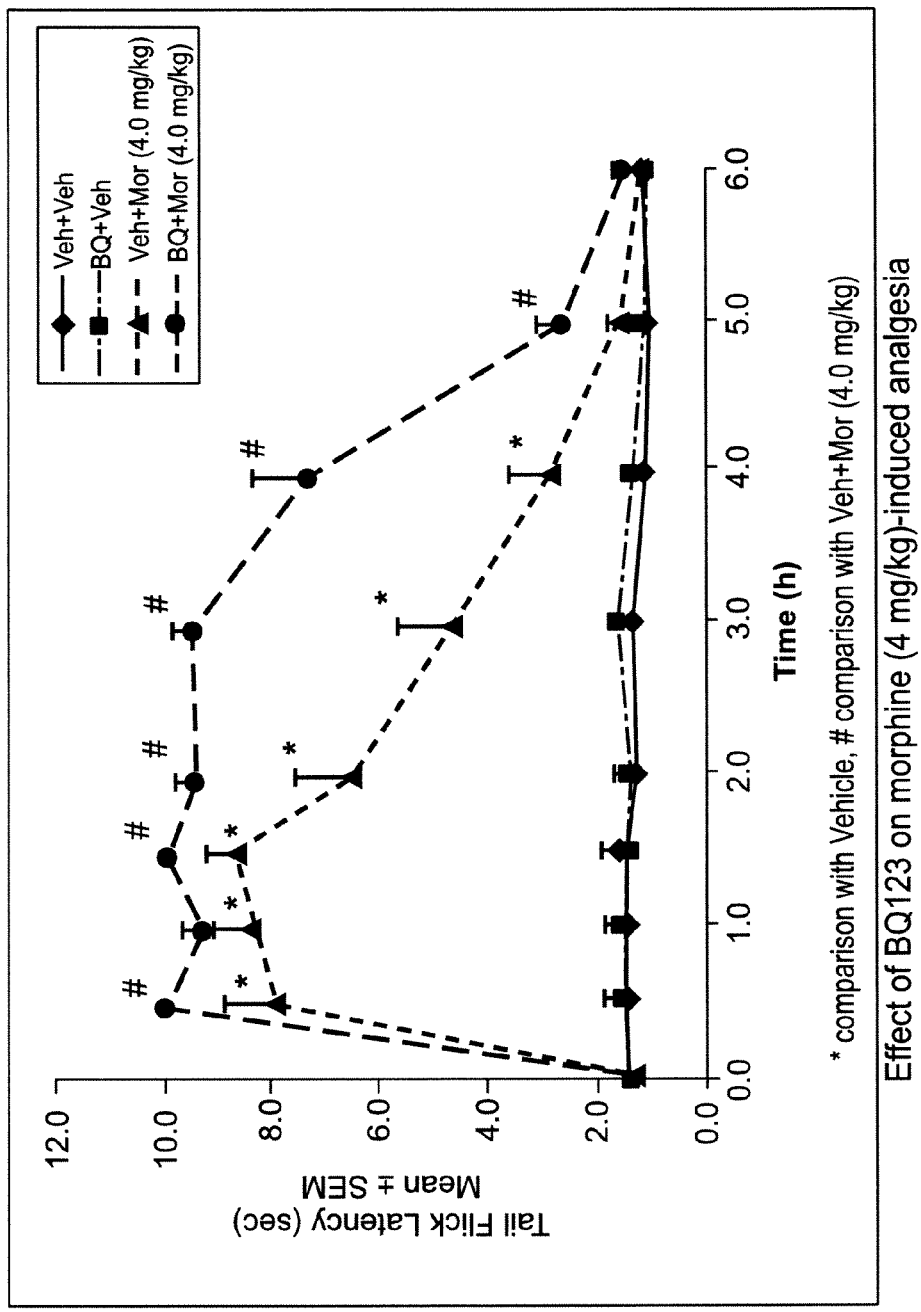
Figure 5:
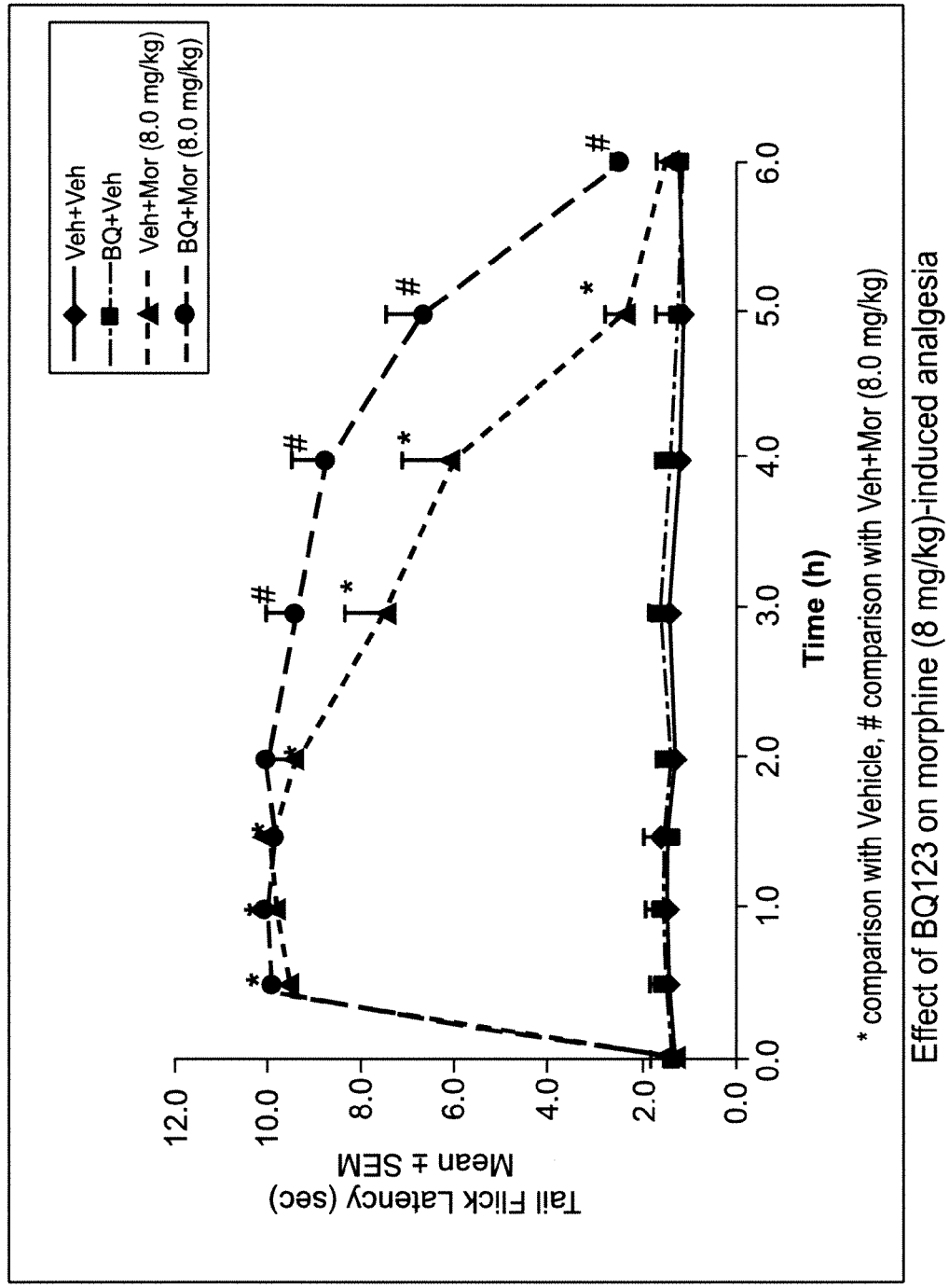

The effect of BQ123 treatment (3 μg, i.c.v.) on morphine analgesia also was determined in mice (FIGS. 3-5). Morphine (2, 4, and 8 mg/kg, s.c.) produced a significant increase in mouse tail flick latency that lasted for 1.5 hours. BQ123 significantly potentiated morphine analgesia, which lasted for more than 4 hours. FIG. 3 especially shows that tail flick latency is increased by administration of BQ123, thereby showing an endothelin antagonist potentiating effect on morphine at a low dosage administration of the opiate analgesic.

Figure 6:
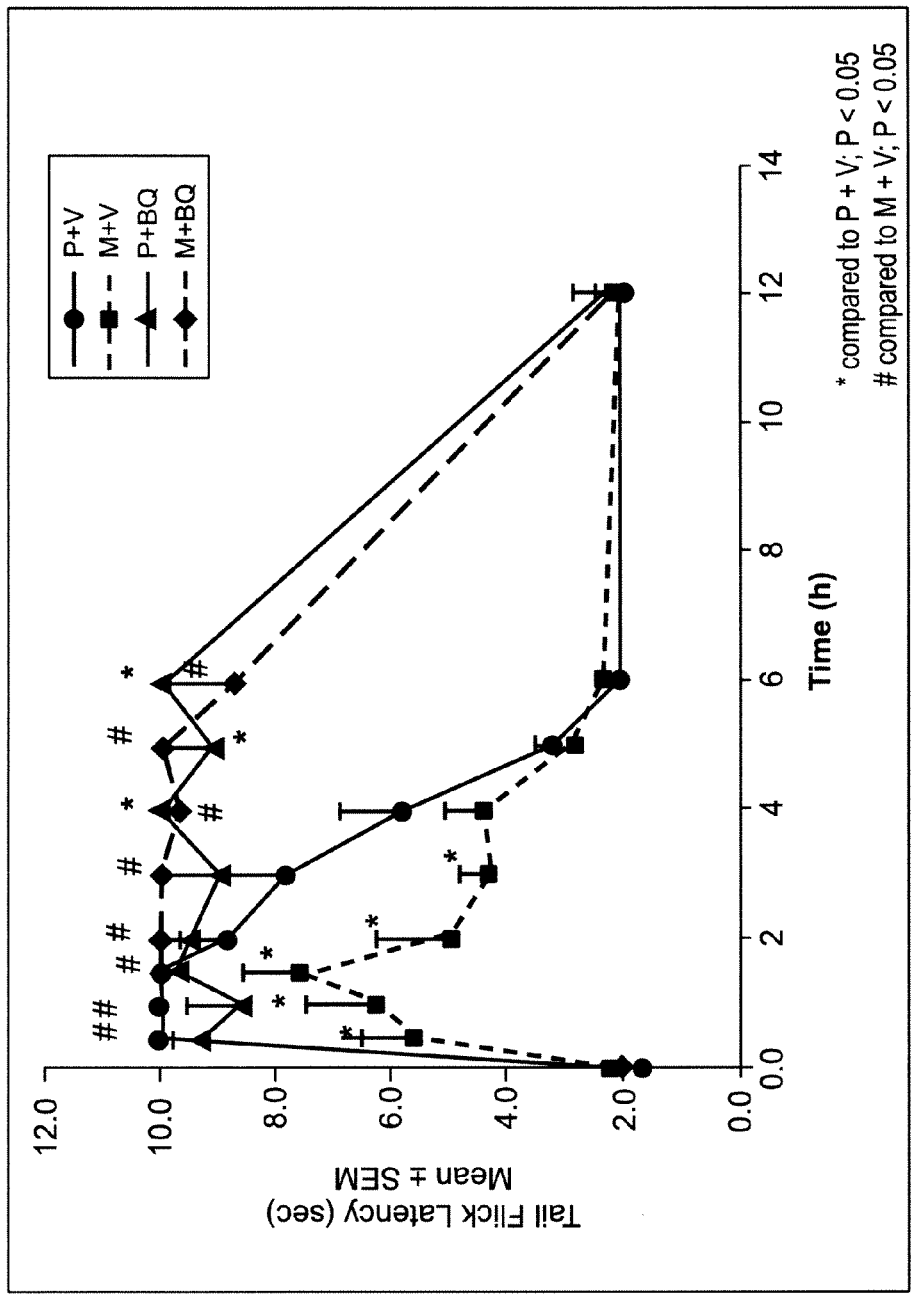
FIGS. 6-8 contain plots showing a reduced morphine tolerance in mice after treatment with the endothelin antagonists BQ123 or BMS182874.
Figure 7:
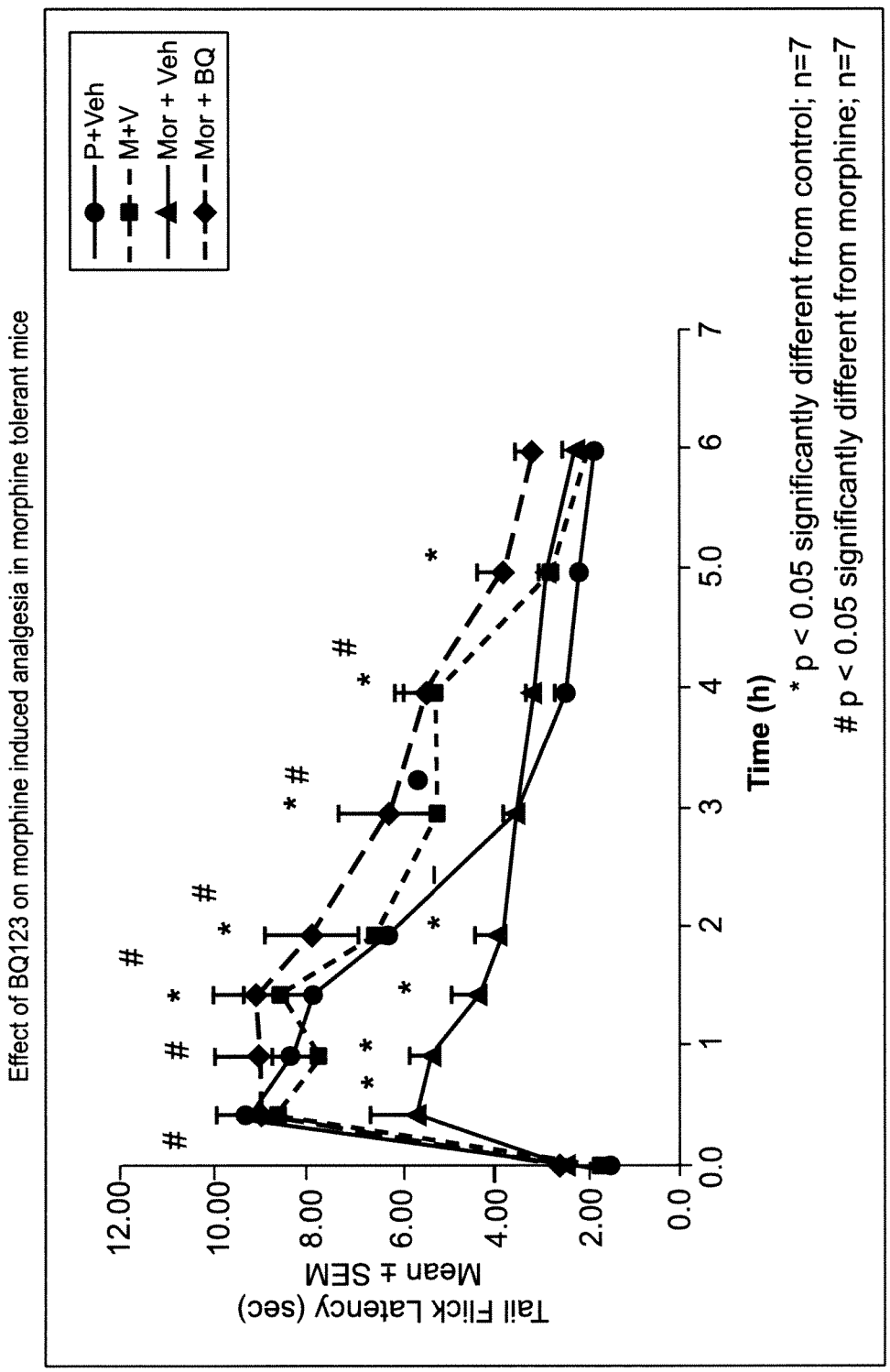
Figure 8:
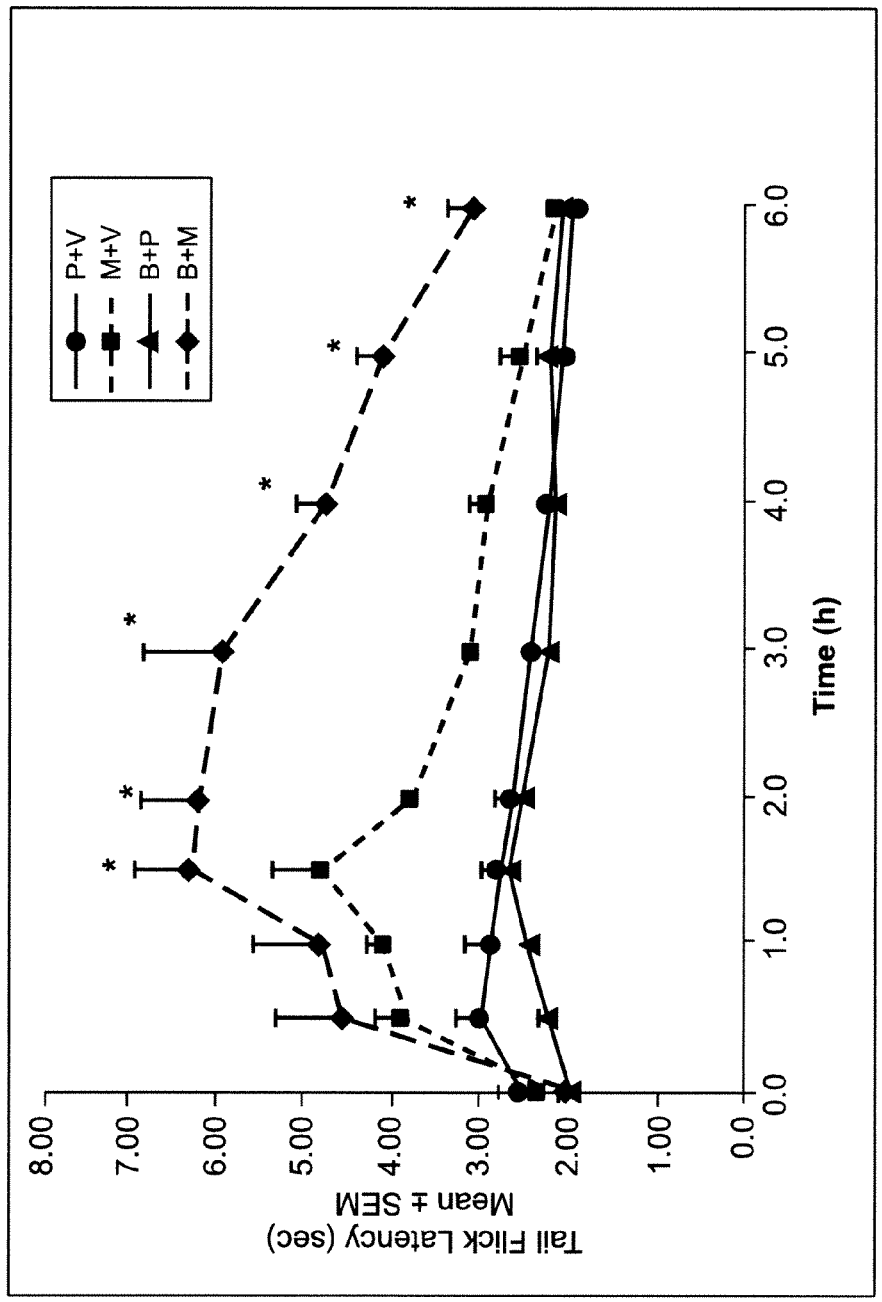

FIGS. 6-8 illustrate the ability of an endothelin antagonist to induce opiate analgesic tolerance in mice and rats rendered tolerant and dependent on morphine. The test method used to generate the data set forth in FIGS. 6-8 is disclosed in H. N. Bhargava et al., *J. Pharmacol. Exp. Ther.*, 252(3), pp. 901-907 (1990). The method disclosed therein was modified slightly for mice because the smaller mice could not survive the morphine dose administered to the rats. Tolerance to morphine is demonstrated in FIGS. 6-8 for the endothelin antagonists BQ123 and BMS182874.

The effect of BQ123 (3 μg, i.c.v.) on naloxone-precipitated morphine withdrawal also was determined in mice. Naloxone (1 mg/kg, i.p.) administration to morphine tolerant mice (1 morphine 75 mg pellet for 3 days) resulted in expression of withdrawal symptoms. BQ123 did not affect hypothermia, loss of body weight, jumping behavior, falls, diarrhea, fecal boli, urination, ptosis, writhing, and rearing behavior during withdrawal. Tests also were performed to determine tolerance to analgesic effect in morphine tolerant dependent rats (6 morphine pellets in 7-day period). BQ123-treated (10 μg, i.c.v., twice a day for 7 days) rats did not become tolerant to morphine.

These studies demonstrate that an endothelin antagonist, like BQ123, potentiates the analgesic effect of morphine and prevents the development of tolerance to morphine analgesia, without affecting naloxone-precipitated morphine withdrawal. The combined use of BQ123 or other ET antagonist and an opiate provides a novel approach to improving analgesia and eliminating morphine tolerance. These findings provide a novel combination of active agents to manage various types of pain.

In summary, rat and mice studies showed that endothelin antagonist administration in combination with an opiate analgesic potentiated analgesia and hyperthermia, but did not affect catalepsy or body weight. A mouse study administering BQ123 and morphine (2, 4, or 8 mg/kg) also showed that analgesia was potentiated, but hypothermia and body weight were not affected.

Another study directed to naloxone (1 mg/kg) initiated withdrawal symptoms in mice in conjunction with a combination morphine and BQ123 treatment showed no effect on temperature, body weight, urination, diarrhea, jumping behavior, number of falls, ptosis, and grooming.

Overall, test results show that an endothelin antagonist significantly potentiates morphine analgesia in mice and rats, prevents the development of tolerance to analgesic actions of opiate analgesics, like morphine, and potentiates morphine-induced hyperthermia in rats, but does not affect morphine-induced hypothermia in mice, does not affect morphine-induced catalepsy in rats, and does not affect naloxone precipitated morphine withdrawal. Therefore, an endothelin antagonist potentiates morphine analgesia, but does not potentiate morphine withdrawal symptoms and prevents or reverses the development of tolerance to analgesic opiates.

The test results clearly demonstrate that endothelin antagonists, like BQ123, potentiate morphine-induced analgesia and hyperthermia without affecting morphine-induced cataleptic behavior. This is an important clinical finding because endothelin antagonists have minimal cardiovascular effects in normal healthy individuals and because ET antagonists, like tezosentan, bosentan, darnsentan, and atrasentan, are nearing regulatory approval. Endothelin antagonists combined with morphine, therefore, can be used to potentiate the analgesic action of morphine without affecting some of the other pharmacological actions of morphine.

It has been demonstrated that ET significantly regulates the central autonomic nervous system (Gulati et al., 1997; Kumar et al., 1997), and most of the withdrawal reactions of morphine also are mediated through the central autonomic nervous system. Central ET modulates pharmacological actions of morphine. Using an ET antagonist together with morphine increases the analgesic and hyperthermic action of morphine, but does not affect the cataleptic action of morphine. On the basis of results obtained, an ET antagonist can reduce the dose of morphine and still produce same degree of analgesic action of morphine as produced by a higher dose of morphine used alone. Lowering the dose of morphine can significantly reduce the addiction potential of morphine in patients.

These findings show that when combined with an endothelin antagonist, morphine and other opiate analgesics produce significant analgesia with a much lower dose of analgesic, and, therefore, the addiction potential of the opiate analgesic is reduced. These observations also indicate that the duration of analgesic response of morphine can be significantly increased by administration of an endothelin antagonist.

The data shows that some morphine-induced pharmacological responses, like change in temperature and analgesia, can be separately potentiated while other responses, like catalepsy, are not affected by endothelin antagonist administration.

The above tests and data show that a combination of an opiate analgesic and an endothelin antagonist can be administered to mammals in methods of treating pain. The opiate analgesic and endothelin antagonist can be formulated in suitable excipients for oral administration, or for parenteral administration. Such excipients are well known in the art. The active agents typically are present in such a composition in an amount of about 0.1% to about 75% by weight, either alone or in combination.

Pharmaceutical compositions containing the active agents, i.e., opiate analgesic and endothelin antagonist, of the present invention are suitable for administration to humans or other mammals. Typically, the pharmaceutical compositions are sterile, and contain no toxic, carcinogenic, or mutagenic compounds that would cause an adverse reaction when administered.

The method of the invention can be accomplished using the active agents as described above, or as a physiologically acceptable salt or solvate thereof. The active agents, salts, or solvates can be administered as the neat compounds, or as a pharmaceutical composition containing either or both entities.

The active agents can be administered by any suitable route, for example by oral, buccal, inhalation, sublingual, rectal, vaginal, intracisternal through lumbar puncture, transurethral, nasal, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™. Administration of the active agents can be performed before, during, or after the onset of pain.

The pharmaceutical compositions include those wherein the active ingredients are administered in an effective amount to achieve their intended purpose. More specifically, a "therapeutically effective amount" means an amount effective to prevent development of, to eliminate, or to alleviate pain. Determination of a therapeutically effective amount is well within the capability of those skilled in the art, especially in light of the detailed disclosure provided herein.

A "therapeutically effective dose" refers to the amount of the active agents that results in achieving the desired effect. Toxicity and therapeutic efficacy of such active agents can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. A high therapeutic index is preferred. The data obtained from such data can be used in formulating a range of dosage for use in humans. The dosage of the active agents preferably lies within a range of circulating concentrations that include the $ED_{50}$ with little or no toxicity. The dosage can vary within this range depending upon the dosage form employed, and the route of administration utilized.

The exact formulation, route of administration, and dosage is determined by an individual physician in view of the patient's condition. Dosage amounts and intervals can be adjusted individually to provide levels of active agents that are sufficient to maintain therapeutic or prophylactic effects.

The amount of active agents administered is dependent on the subject being treated, on the subject's weight, the severity of the affliction, the manner of administration, and the judgment of the prescribing physician.

Specifically, for administration to a human in the curative or prophylactic treatment of pain, oral dosages of an opiate analgesic and endothelin antagonist, individually generally are about 10 to about 200 mg daily for an average adult patient (70 kg), typically divided into two to three doses per day. Thus, for a typical adult patient, individual tablets or capsules contain about 0.1 to about 200 mg opioid analgesic and about 0.1 to about 50 mg endothelin antagonist, in a suitable pharmaceutically acceptable vehicle or carrier, for administration in single or multiple doses, once or several times per day. Dosages for intravenous, buccal, or sublingual administration typically are about 0.1 to about 10 mg/kg per single dose as required. In practice, the physician determines the actual dosing regimen that is most suitable for an individual patient, and the dosage varies with the age, weight, and response of the particular patient. The above dosages are exemplary of the average case, but there can be individual instances in which higher or lower dosages are merited, and such are within the scope of this invention.

The active agents of the present invention can be administered alone, or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the active agents into preparations that can be used pharmaceutically.

These pharmaceutical compositions can be manufactured in a conventional manner, e.g., by conventional mixing, dissolving, granulating, dragee-making, emulsifying, encapsulating, entrapping, or lyophilizing processes. Proper formulation is dependent upon the route of administration chosen. When a therapeutically effective amount of the active agents are administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% of an active agent of the present invention, and preferably from about 25% to about 90% of an active agent of the present invention. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.5% to about 90% by weight of active agents, and preferably about 1% to about 50% of an active agents.

When a therapeutically effective amount of the active agents is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

Suitable active agents can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the active agents with a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

The active agents can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents, such as suspending, stabilizing, and/or dispersing agents.

Pharmaceutical compositions for parenteral administration include aqueous solutions of the active agent in water-soluble form. Additionally, suspensions of the active agents can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

The active agents also can be formulated in rectal compositions, such as suppositories or retention enemas, e.g., containing conventional suppository bases. In addition to the formulations described previously, the active agents also can be formulated as a depot preparation. Such long-acting formulations can be administered by implantation (for example, subcutaneously or intramuscularly) or by intramuscular injection. Thus, for example, the active agents can be formulated with suitable polymeric or hydrophobic materials (for example, as an emulsion in an acceptable oil) or ion exchange resins, or as sparingly soluble derivatives, for example, as a sparingly soluble salt.

In particular, the active agents can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. An active agent also can be injected parenterally, for example, intravenously, intramuscularly, subcutaneously, intrathecally, intracisternally, or intracoronarily. For parenteral administration, the active agent is best used in the form of a sterile aqueous solution which can contain other substances, for example, salts, or monosaccharides, such as mannitol or glucose, to make the solution isotonic with blood.

For veterinary use, the active agents are administered as a suitably acceptable formulation in accordance with normal veterinary practice. The veterinarian can readily determine the dosing regimen and route of administration that is most appropriate for a particular animal.

As stated above, morphine is one of the most potent analgesics, and is widely used for pain management in several disease conditions, including cancer. A major problem in the use of morphine, and other opiate analgesics, is their potential to produce sedation tolerance/dependent, and respiratory depressions, and to cause addiction.

It has been discovered that using an endohelin antagonist in combination with an opiate analgesic potentiates the analgesic and hyperthemic action of the analgesic, but does not increase the sedative or cataleptic action of the analgesic. The combined opiate analgesic-endothelin antagonist treatment can be used, for example, in office surgeries, oral surgeries, and post-surgical pain management.

It also has been discovered that by using an endothelin antagonist together with an opiate analgesic, the dose of morphine can be reduced, and still provide the same analgesic action as a larger dose of morphine used alone. By using less morphine, the addiction potential of an opiate analgesic in patients can be reduced significantly. The administration of an endothelin antagonist to an individual undergoing opiate analgesic treatment, therefore, reduces or eliminates tolerance to opiate analgesics.

REFERENCES

M. D. Aceto et al., *Eur J Pharmacol,* 123(3):387-93 (1986).
P. Avenet et al., *Neurosci Lett,* 223(2):133-6 (1997).
A. Cowan et al., *J Pharmacol Exp Ther,* 246(3):950-5 (1988).
G. Davar et al., *Neuroreport,* 9(10):2279-83 (1998).
G. E. DeLander et al., *J Pharmacol Exp Ther,* 23/(1):91-6 (1984).
K. M. Foley, Handbook of Experimental Pharmacology, Springer-Verlag, Berlin (1993).
Y. Fukagawa et al., *Eur J Pharmacol,* 170(1-2):47-51 (1989).
R. R. Goodman et al., *Proc Natl Acad Sci USA,* 82(19):6667-71 (1985).
F. J. Gordon et al., *J Pharmacol Exp Ther,* 237(2):428-36 (1986).
F. J. Gordon, *Peptides,* 11(2):305-9 (1990).
A. Gulati et al., *Life Sci,* 58(5):437-45 (1996).
A. Gulati et al., *Life Sci,* 51(22):1715-24 (1992).
A. Gulati et al., *Am J Physiol,* 273(3 Pt 2):H1177-86 (1997).
A. Gulati et al., *J Cardiovasc Pharmacol,* 26(Suppl 3):S244-6 (1995).

A. Gulati et al., *Drug Develop Res*, 26:361-387 (1992).
H. Hama et al., *Biochem Biophys Res Commun*, 186(1):355-62 (1992).
K. A. Hickey et al., *Am J Physiol*, 248(5 Pt 1):C550-6 (1985).
Himmelsbach, *Fed Proc*, 2:201-203 (1943).
M. Ihara et al., *Life Sci*, 50(4):247-55 (1992)
M. F. Jarvis et al., *Eur J Pharmacol*, 388(1):29-35 (2000).
Q. Jiang et al., *Prog Clin Biol Res*, 328:449-52 (1990).
J. L. Katz et al., Behavioral Analysis of Drug Dependence, ed. S. R. Goldberg et al., Vol. Ch. 8, pp. 287-327, Academic Press, Orlando (1986).
Y. Kawano et al., *J Hypertens Suppl* 7(6):S22-3 (1989).
S. Koyama et al., *Eur J Pharmacol*, 90(4):367-76 (1983).
A. Kumar et al., *Peptides*, 18(6):855-64 (1997).
T. Kuwaki et al., *Jpn J Physiol*, 44(1):1-18 (1994).
M. W. MacCumber et al., *Proc Natl Acad Sci USA*, 87(6): 2359-63 (1990).
R. Maldonado et al., *J Pharmacol Exp Ther*, 26/(2):669-77 (1992).
R. Maldonado et al., Neurobiological Mechanisms of Opiate Withdrawal, ed. R. Maldonado et al., Vol. Ch. 5, pp. 77-124, Springer, N.Y. (1996).
K. Matsumura et al., *Am J Physiol*, 266(4 Pt 2):R1403-10 (1994).
K. Matsumura et al., *Hypertension*, 19(6 Pt 2):648-52 (1992).
K. Matsumura et al., *Hypertension*, 17(6 Pt 2):1192-6 (1991).
H. W. Matthes et al., *Nature*, 383(6603): 819-23 (1996).
C. N. May et al., *Clin Sci (Colch)*, 76(4):431-7 (1989).
H. D. Modanlou et al., *Can J Physiol Pharmacol*, 76(4):443-50 (1998).
A. S. Moskowitz et al., *Brain Res*, 360(1-2):108-16 (1985).
M. Narita et al., *Pharmacol Ther*, 89(1):1-15 (2001).
M. Narita et al., *Psychopharmacology*, 111(4):423-6 (1993).
Y. Ouchi et al., *Am J Physiol*, 256(6 Pt 2):H1747-51 (1989).
U. Pagotto et al., *J Cardiovasc Pharmacol*, 26(Suppl 3):S104-6 (1995).
Z. Z. Pan, *Trends Pharmacol Sci*, 19(3):94-8 (1998).
G. W. Pasternak et al., *J Med Chem*, 23(6):674-6 (1980).
A. Pfeiffer et al., *Endocrinology*, 113(3):929-38 (1983).
P. S. Portoghese et al., *J Med Chem*, 23(3):233-4 (1980).
C. P. Quock et al., *Br J Addict Alcohol Other Drugs*, 63:261-270 (1968).
R. B. Raffa et al., *Life Sci*, 54(4):L57-62 (1994).
S. Rebello et al., *Brain Res*, 676(1):141-50 (1995).
E. E. Reynolds et al., *Biochem Biophys Res Commun*, 160(2): 868-73 (1989).
T. Sakurai et al., *Nature*, 348(6303):732-5 (1990).
D. G. Standaert et al., *J Comp Neurol*, 343(1):1-16 (1994).
P. D. Stein et al., *J Med Chem*, 37(3):329-31 (1994).
T. Suzuki et al., *Life Sci*, 50(12):849-56 (1992a).
T. Suzuki et al., *Eur J Pharmacol*, 213(1):91-7 (1992b).
T. Suzuki et al., *Pharmacol Biochem Behav*, 57(1-2):293-9 (1997).
A. E. Takemori et al., *Eur J Pharmacol*, 70(4):445-51 (1981).
T. M. Tzschentke et al., *Neurosci Lett*, 193(1):37-40 (1995).
J. M. Van Ree et al., *Pharmacol Rev*, 51:342-396 (1999).
M. A. Varney et al., *J Pharmacol Exp Ther*, 279(1):367-78 (1996).
S. J. Ward et al., *J Pharmacol Exp Ther*, 220:494-498 (1982).
M. Watanabe et al., *J Comp Neurol*, 338:377-390 (1993).
J. T. Williams et al., *Physiol Rev*, 81(1):299-343 (2001).
M. Yanagisawa et al., *J Hypertens Suppl* 6(4):S188-91 (1988).

Modifications and variations of the invention as hereinbefore set forth can be made without departing from the spirit and scope thereof, and, therefore, only such limitations should be imposed as are indicated by the appended claims.

APPENDIX A
SELECTIVE ET$_A$ ANTAGONISTS

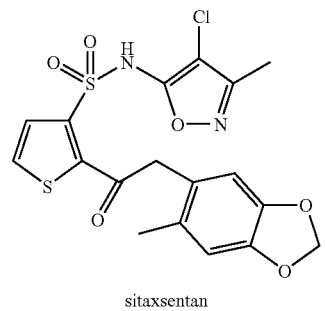

sitaxsentan

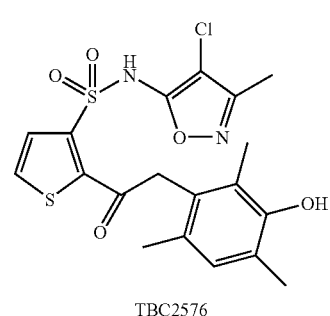

TBC2576

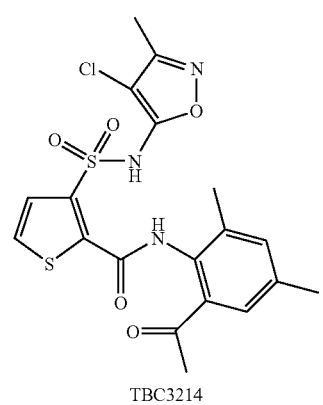

TBC3214

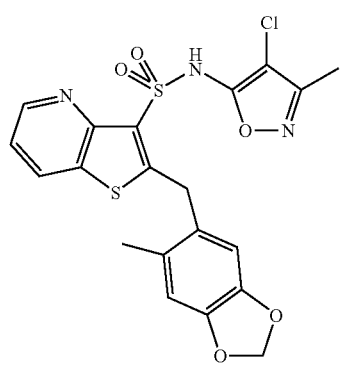

-continued
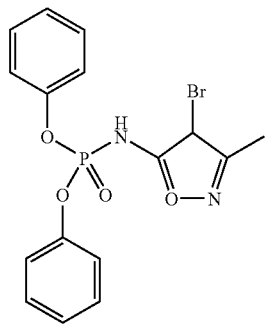
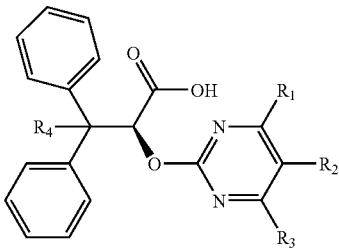
6 R₁ = R₃ = R₄ = CH₃, R₂ = H
7 R₁ = R₃ = R₄ = OCH₃, R₂ = F
8 R₁ = OCH₃, R₂ = H, R₃ = CH₃,
  R₄ = —OCH₂CON(CH₃)C₆H₅
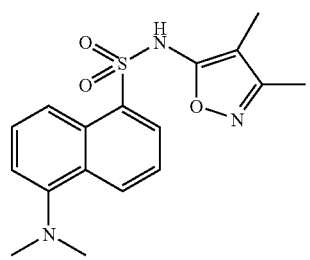
BMS 182,874
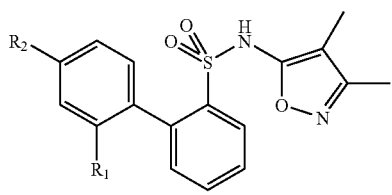
10 R₁ = CH₂OH, R₂ = H
11 R₁ = H, R₂ = 2-oxazolyl
12 R₁ = H, R₂ = 2-pyrimidinyl
13 R₁ = H, R₂ = 4-methoxyethoxymethyl-
   4-oxo-1,2,4-triazol-2-yl
14 R₁ = H, R₂ = 1,3-diazo-2-butyl-4-
   oxospiro(4,4)-1-nonen-3-ylmethyl
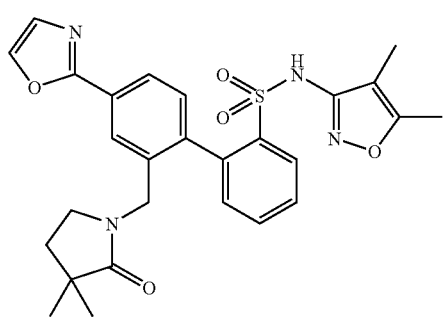
-continued
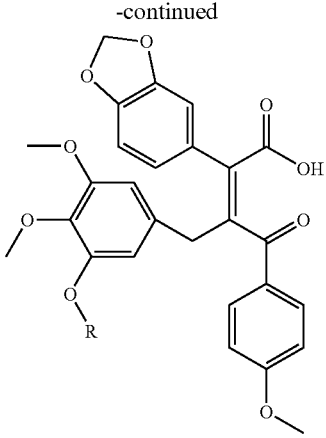
16 R = CH₃ (PD156707)
17 R = CH₂CH₂CH₂SO₃H
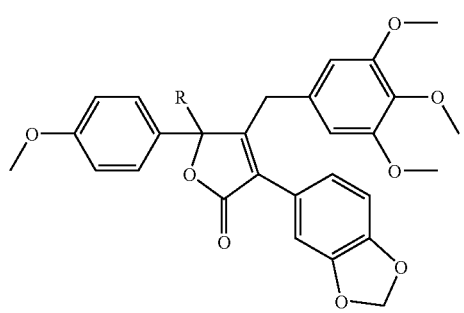
18 R = OCH₂CH₂CH₂SO₃H
19 R = OCONHCH₂CO₂C₂H₅
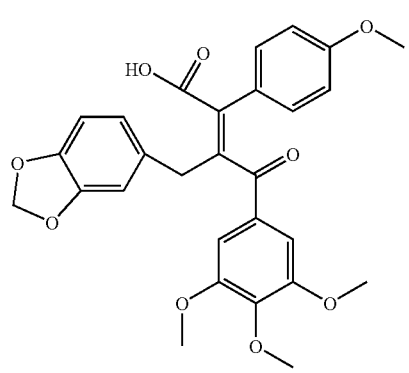
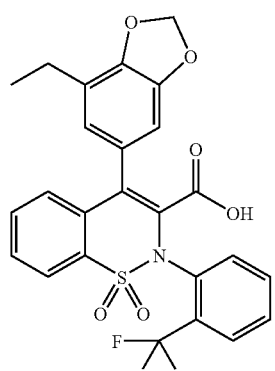
PD180988

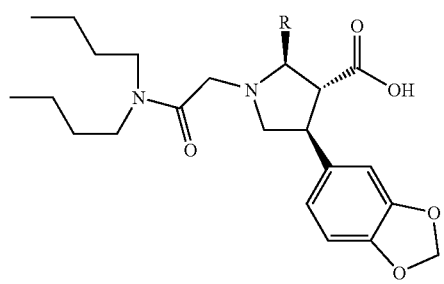
22 R = C$_6$H$_4$-4-OCH$_3$ (ABT-627)
23 R = CH$_2$CH$_2$-2-pyridyl
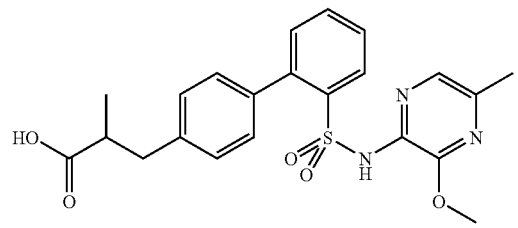
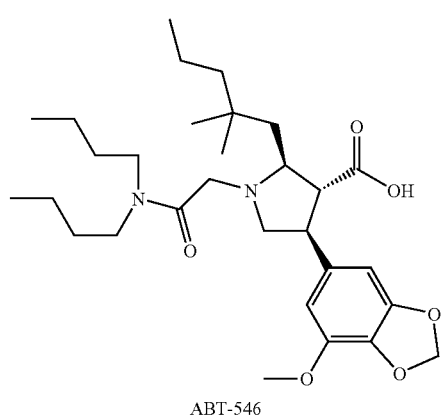
ABT-546
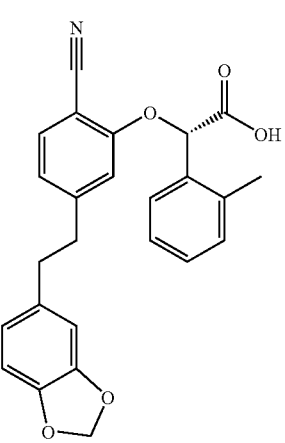
RPR118031A
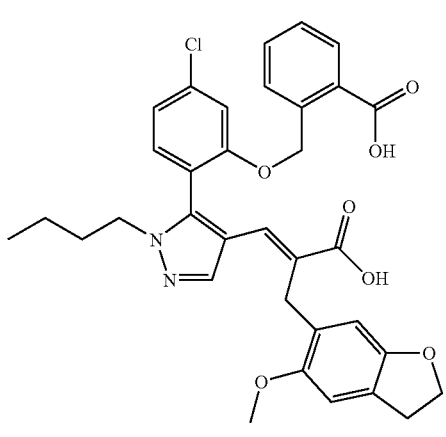
SB247083
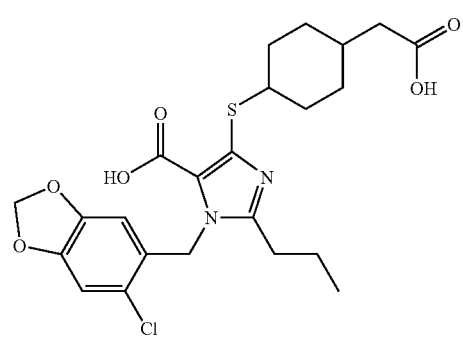
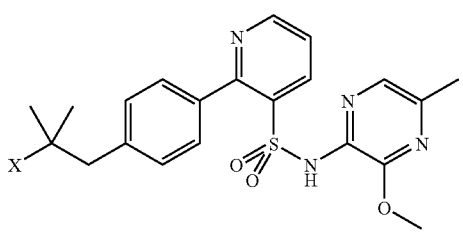
26 X = CO$_2$H (Z1611)
27 X = H
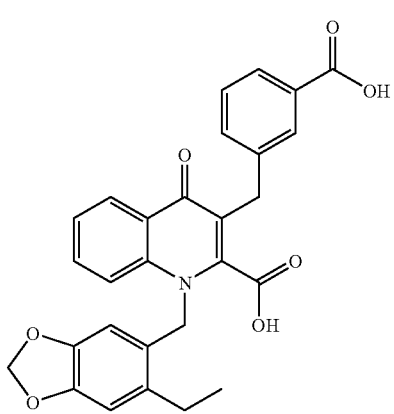

-continued
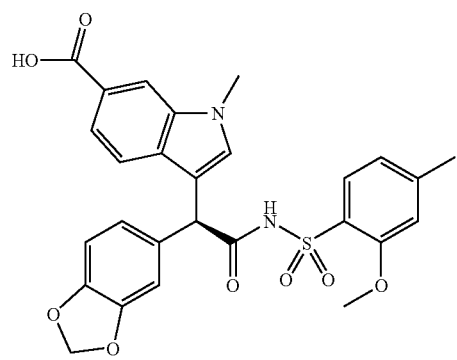
32
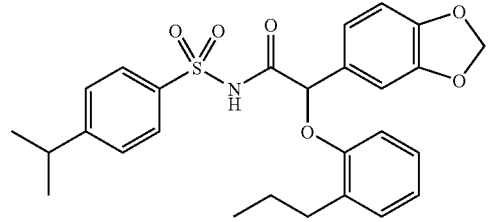
33
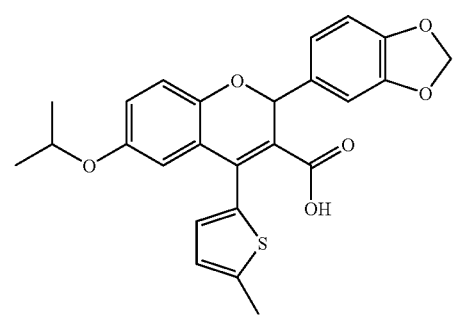
34
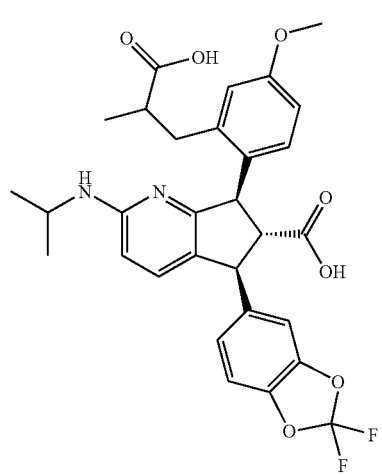
35
APPENDIX B
BALANCED ET$_A$/ET$_B$ ANTAGONISTS
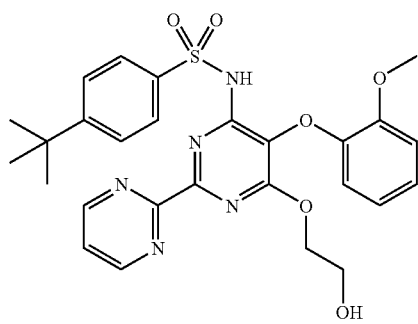
bosentan
46
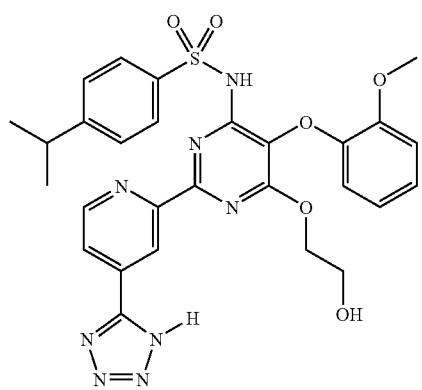
47
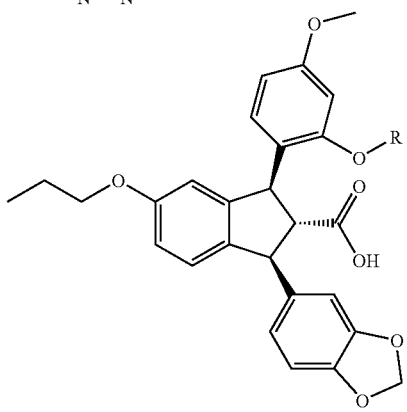
48 R = CH$_2$CO$_2$H SB209670
49 R = CH$_2$CH$_2$OH SB217242
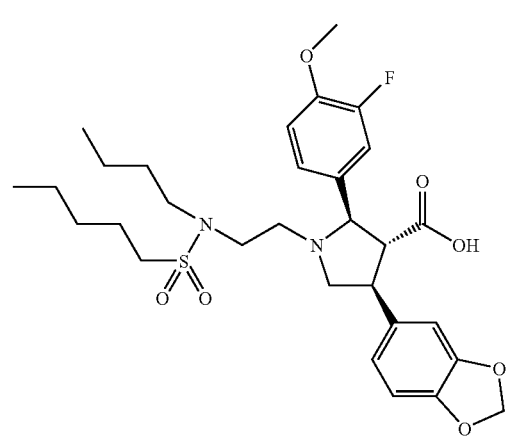
50

-continued
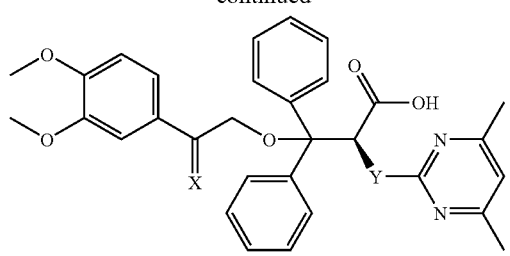
51 X = H₂, Y = CH₂ S-LU 302872
52 X = O, Y = O
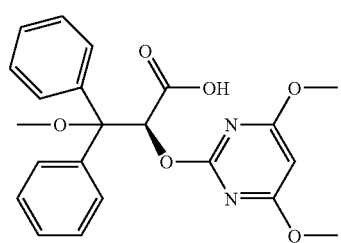
53
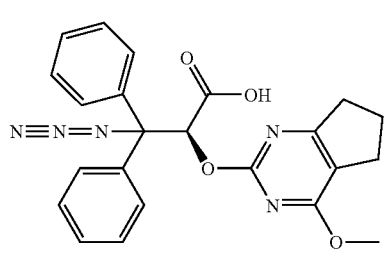
54
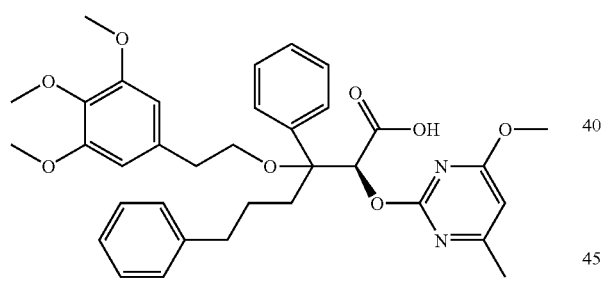
55
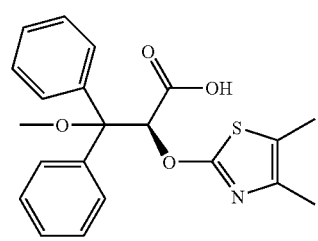
56
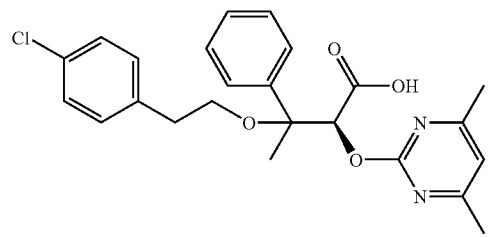
57
-continued
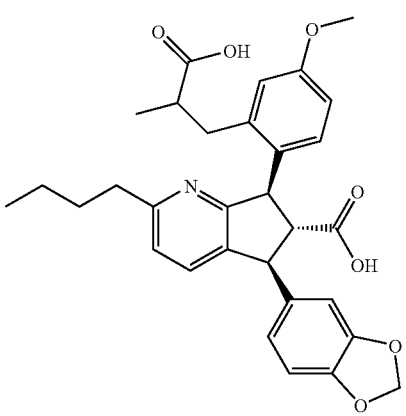
58
J-104132
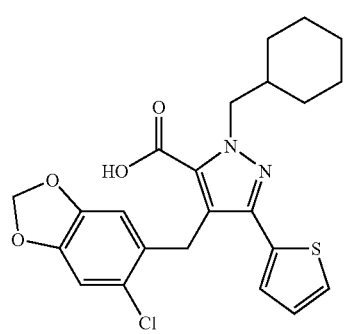
59
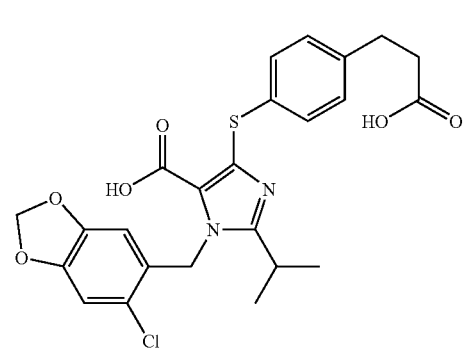
60
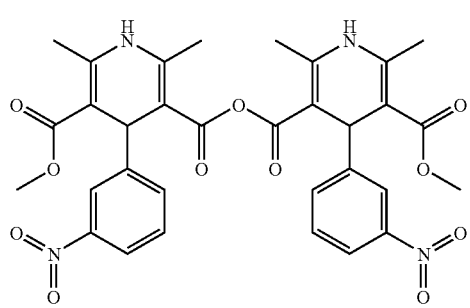
61

27
-continued
62
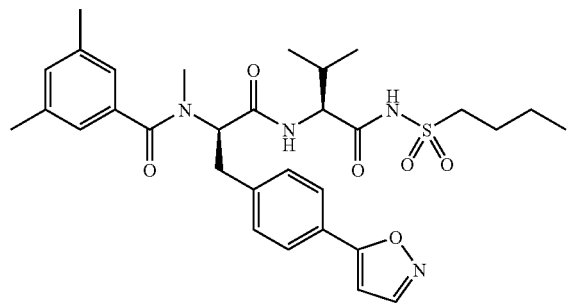
63
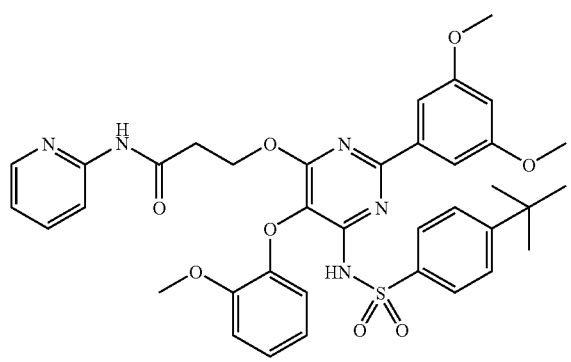
64
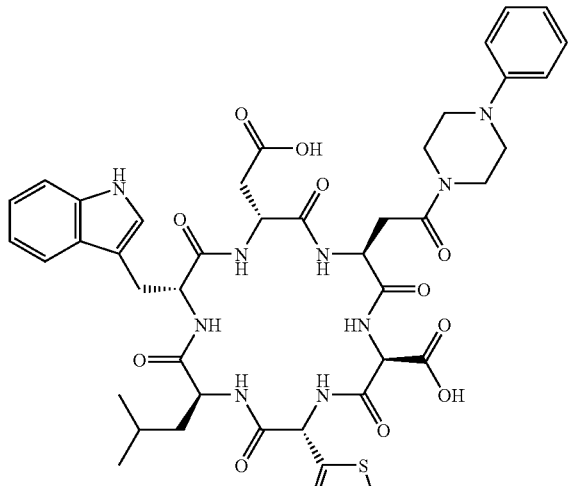
TAK-044
28
-continued
65
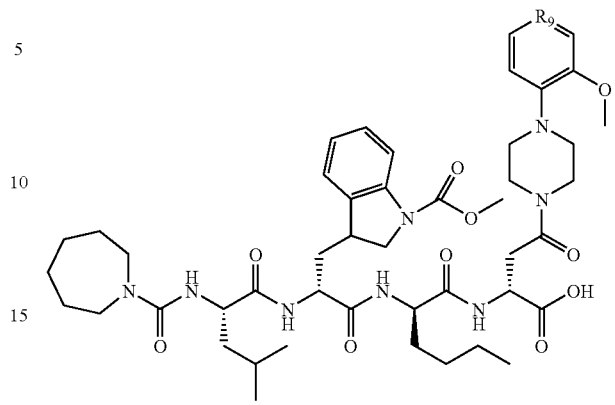
66
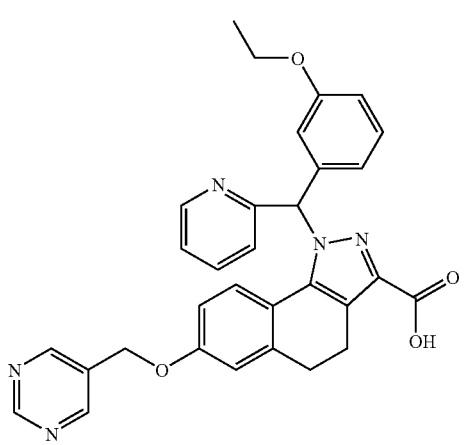
67

APPENDIX C
SELECTIVE ET_B ANTAGONISTS
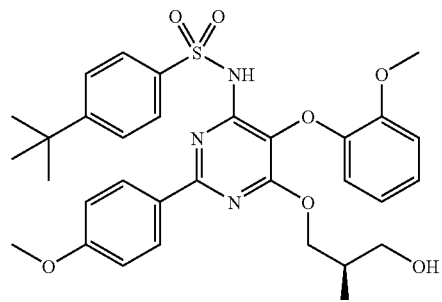
Ro 46-8443
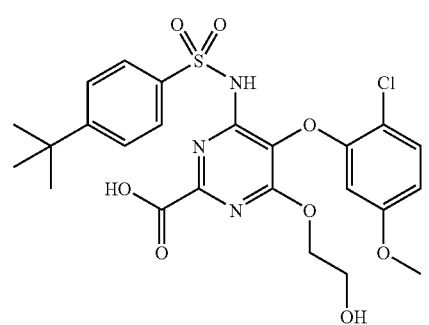
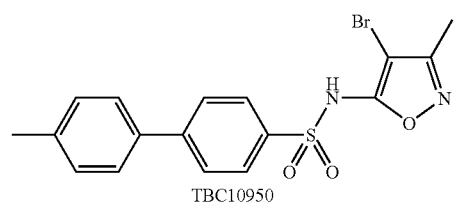
TBC10950
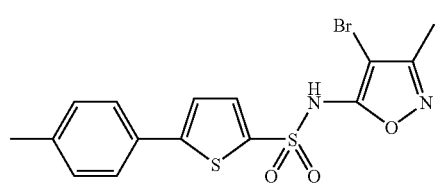
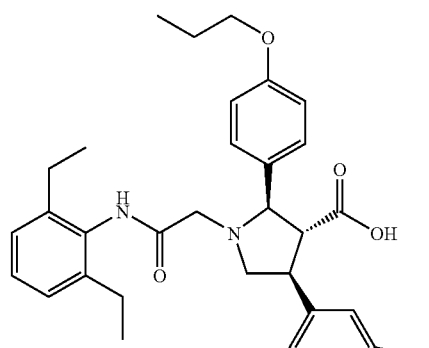
A192621
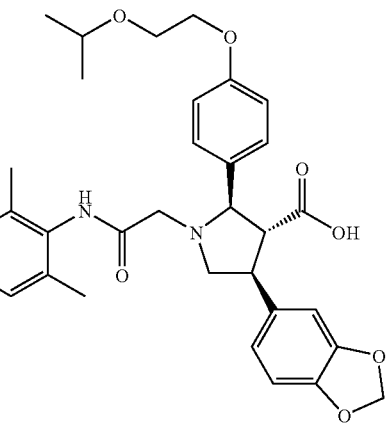
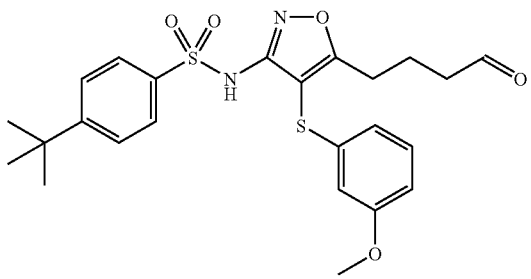
43 X = O
44 X = NNHCO-3-pyridyl
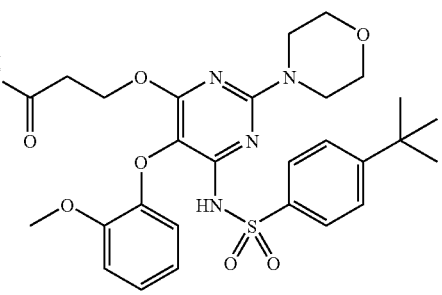

APPENDIX D
MISCELLANEOUS ET ANTAGONISTS
68
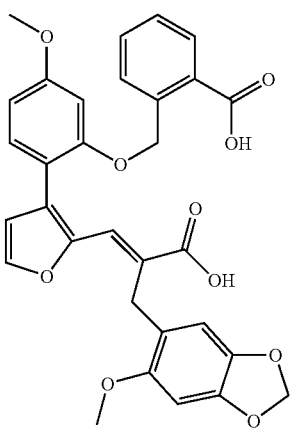
69
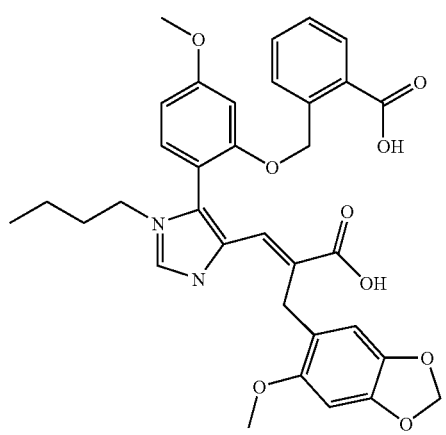
70
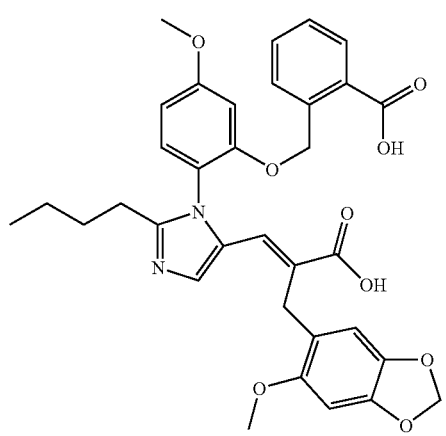
71
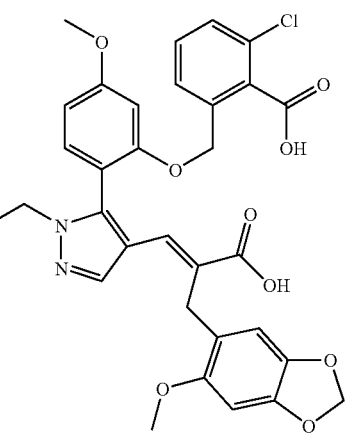
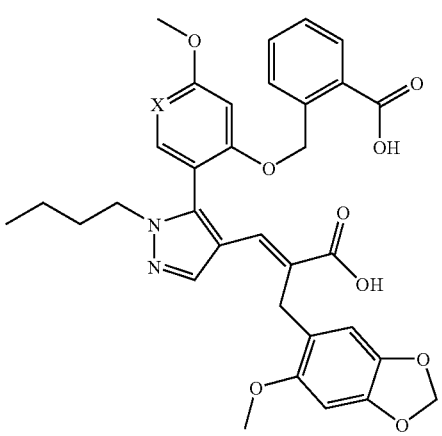
72 X = C
73 X = N
74
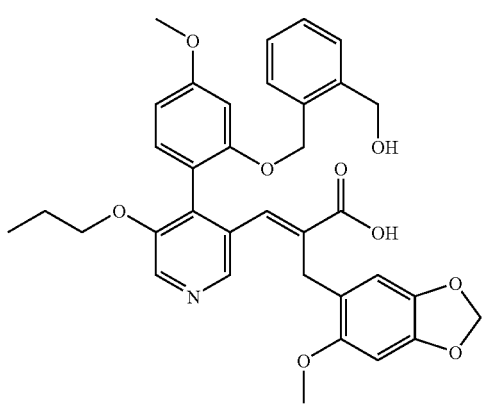

75
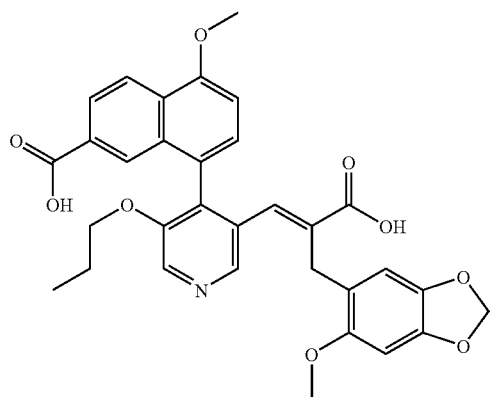
76
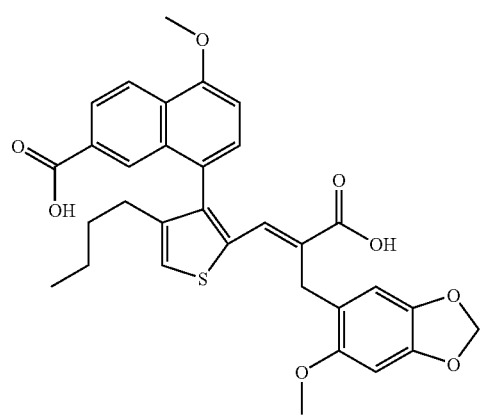
77
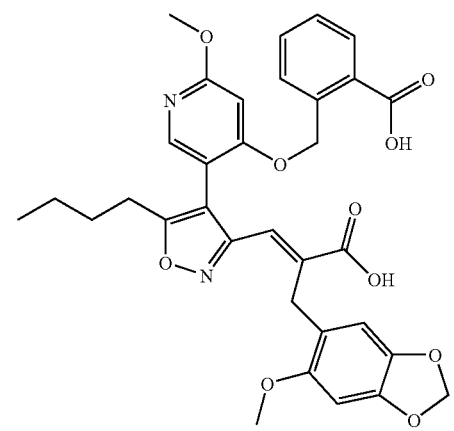
78
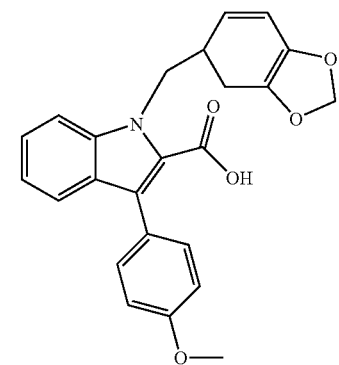
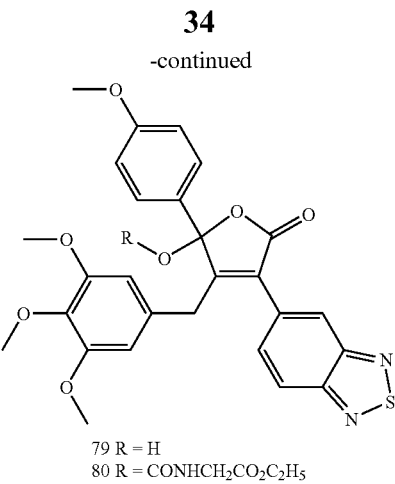
79 R = H
80 R = CONHCH₂CO₂C₂H₅
81
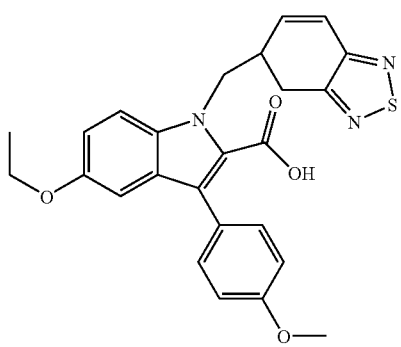
82
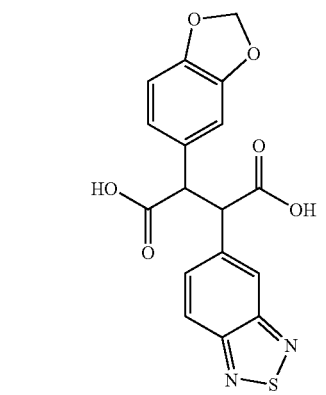
83
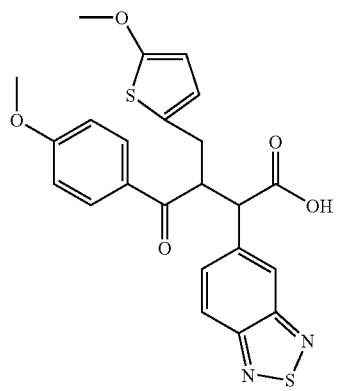

84
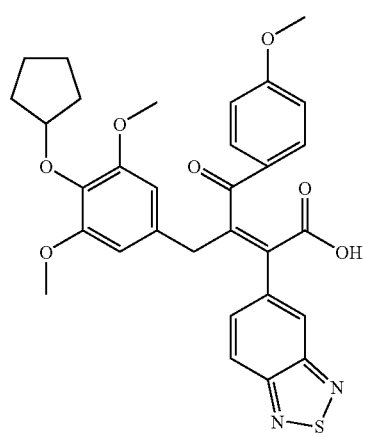
85
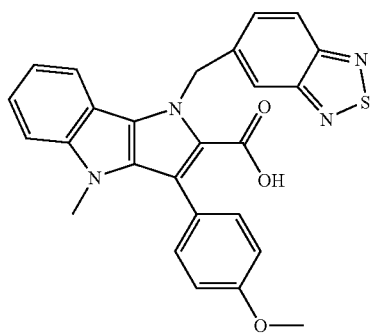
86
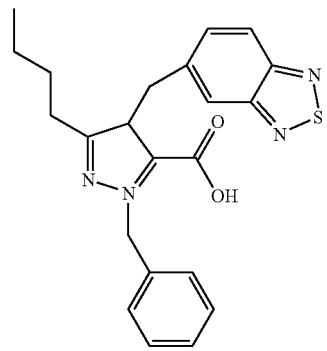
87
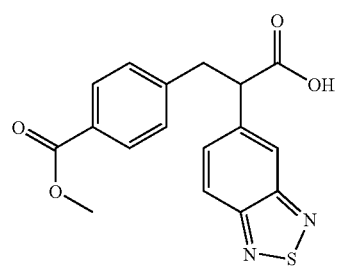
88
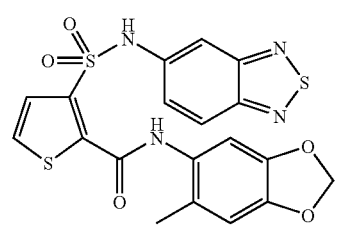
89
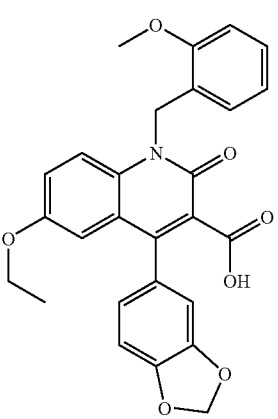
90
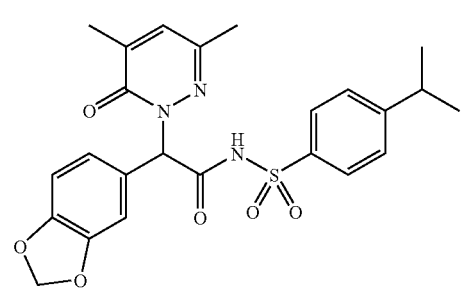
91
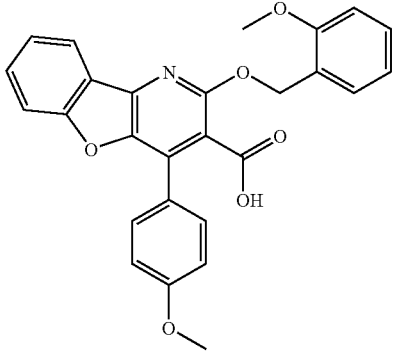
92
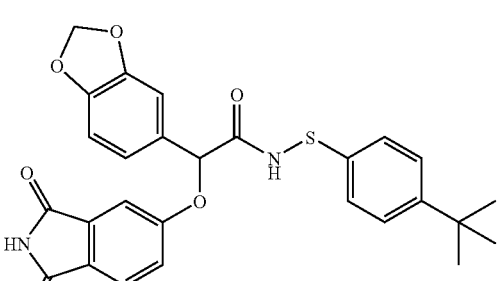
93
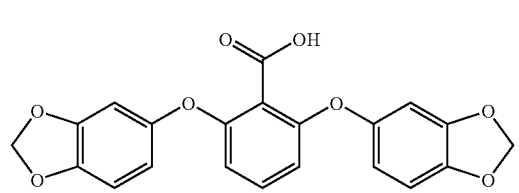

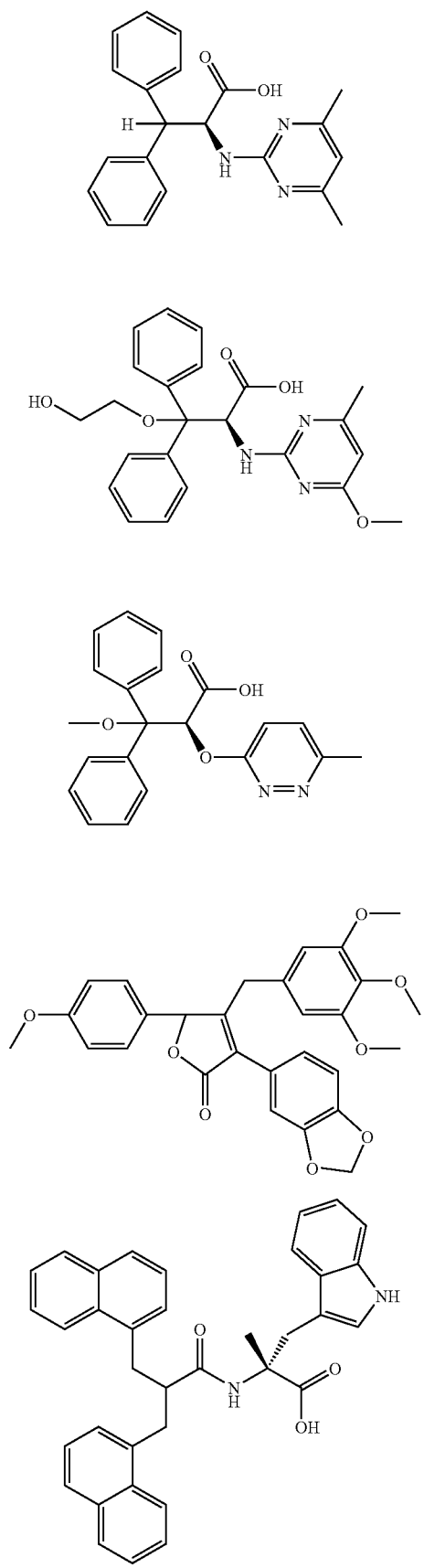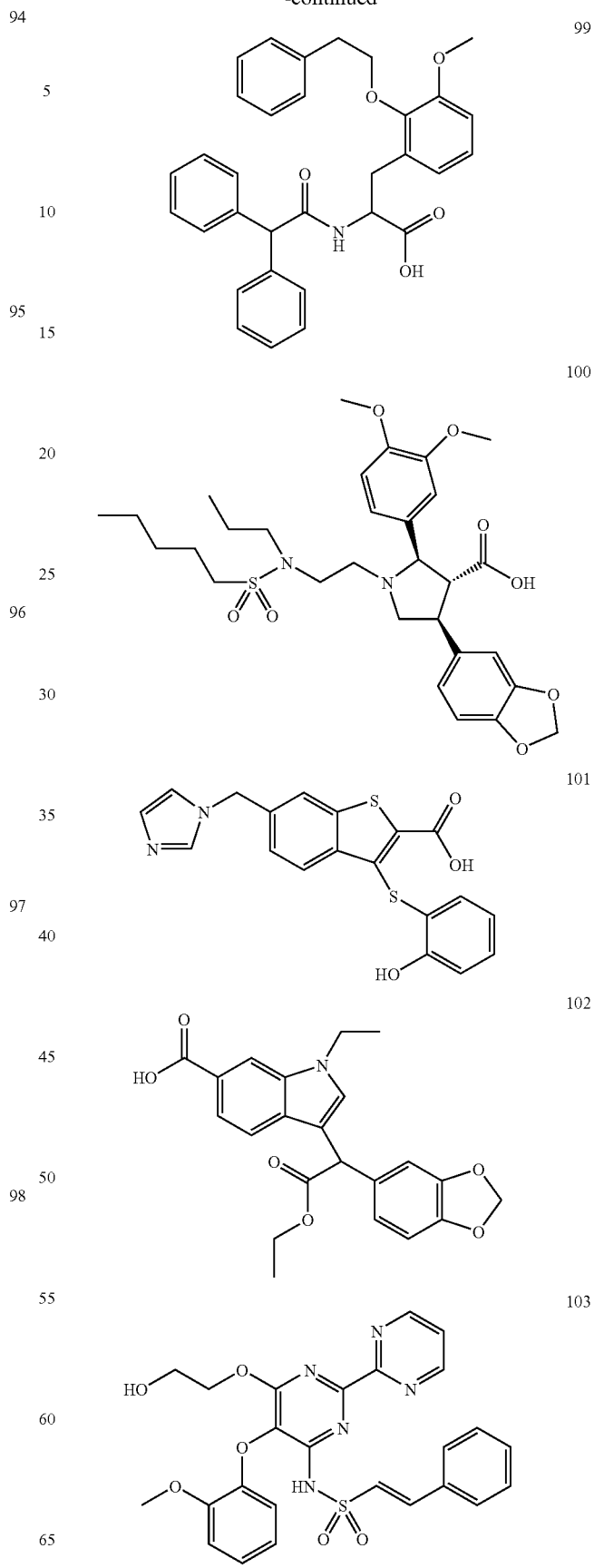

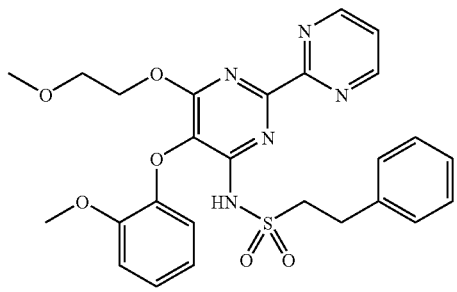

104

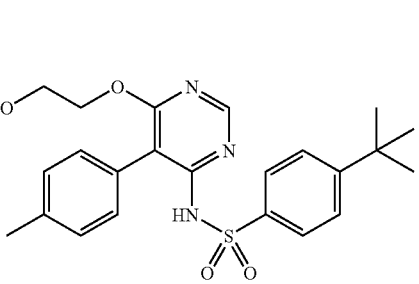

108

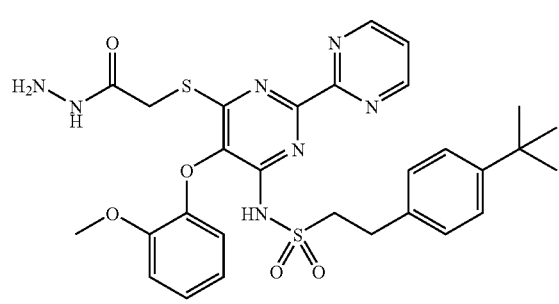

105

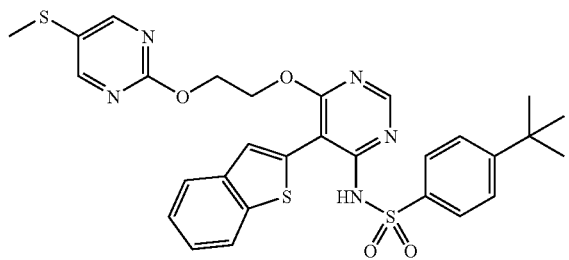

109

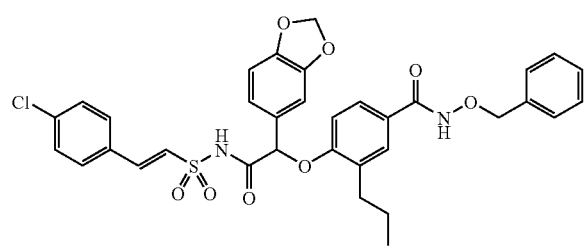

106

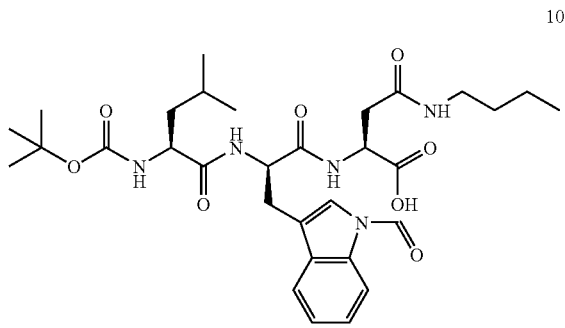

107

What is claimed is:

1. A method of treating symptoms of opiate analgesic withdrawal in an individual undergoing opiate analgesic therapy comprising administering a therapeutically effective amount of a specific endothelin-A antagonist, wherein the specific endothelin-A antagonist is BQ123, the opiate analgesic is selected from the group consisting of morphine, a salt thereof, and oxycodone hydrochloride, and the symptoms are selected from the group consisting of weight loss, nasal discharge, lacrimation, chills, enhanced motor reflexes, hyperthermia, hyperventilation, emesis and diarrhea.

2. The method of claim 1 wherein the opiate analgesic and endothelin antagonist are administered simultaneously.

3. The method of claim 2 wherein the opiate analgesic and endothelin antagonist are administered from a single composition.

4. The method of claim 2 wherein the opiate analgesic and endothelin antagonist are administered from separate compositions.

5. The method of claim 1 wherein the opiate analgesic and endothelin antagonist are administered sequentially.

6. The method of claim 5 wherein the opiate analgesic is administered prior to the endothelin antagonist.

7. The method of claim 5 wherein the endothelin antagonist is administered prior to the opiate analgesic.

8. The method of claim 1 wherein the individual is a human.

* * * * *